(12) United States Patent
Tan et al.

(10) Patent No.: US 11,266,604 B2
(45) Date of Patent: Mar. 8, 2022

(54) HIGHLY STABLE NON-VESICULAR NANOPARTICLES AND APPLICATION THEREOF IN TREATING MICROBIAL INFECTION

(71) Applicant: ALAYA (SHANGHAI) BIOSCIENCE CO., LTD, Shanghai (CN)

(72) Inventors: Yun Tan, Shanghai (CN); Gang Wang, Shanghai (CN)

(73) Assignee: ALAYA (SHANGHAI) BIOSCIENCE CO., LTD., Shanghai (CN)

( * ) Notice: Subject to any disclaimer, the term of this patent is extended or adjusted under 35 U.S.C. 154(b) by 40 days.

(21) Appl. No.: 15/760,491

(22) PCT Filed: Sep. 14, 2016

(86) PCT No.: PCT/CN2016/099136
§ 371 (c)(1),
(2) Date: Mar. 15, 2018

(87) PCT Pub. No.: WO2017/045628
PCT Pub. Date: Mar. 23, 2017

(65) Prior Publication Data
US 2018/0250228 A1 Sep. 6, 2018

(30) Foreign Application Priority Data
Sep. 17, 2015 (CN) .......................... 201510594983.0

(51) Int. Cl.
| | | |
|---|---|---|
| *A61K 9/107* | (2006.01) | |
| *A61K 31/20* | (2006.01) | |
| *A61K 31/201* | (2006.01) | |
| *A61K 31/202* | (2006.01) | |
| *A61K 9/16* | (2006.01) | |
| *A61K 31/19* | (2006.01) | |
| *A61K 47/54* | (2017.01) | |
| *A61P 31/04* | (2006.01) | |
| *A61P 31/10* | (2006.01) | |
| *A61K 47/14* | (2017.01) | |
| A61K 31/16 | (2006.01) | |
| A61K 31/397 | (2006.01) | |

(52) U.S. Cl.
CPC ............ *A61K 9/1617* (2013.01); *A61K 9/107* (2013.01); *A61K 9/1075* (2013.01); *A61K 9/16* (2013.01); *A61K 31/19* (2013.01); *A61K 31/20* (2013.01); *A61K 47/14* (2013.01); *A61K 47/542* (2017.08); *A61P 31/04* (2018.01); *A61P 31/10* (2018.01); A61K 31/16 (2013.01); A61K 31/397 (2013.01); A61K 2300/00 (2013.01)

(58) Field of Classification Search
None
See application file for complete search history.

(56) References Cited

U.S. PATENT DOCUMENTS

| | | | | | |
|---|---|---|---|---|---|
| 4,880,634 | A | * | 11/1989 | Speiser | A61K 9/5123 424/450 |
| 5,250,236 | A | * | 10/1993 | Gasco | A61K 9/5123 264/4.3 |
| 2010/0305218 | A1 | | 12/2010 | Wooster et al. | |
| 2011/0028546 | A1 | | 2/2011 | Kumar | |
| 2012/0289591 | A1 | | 11/2012 | Folan | |
| 2015/0224054 | A1 | | 8/2015 | Bell et al. | |

FOREIGN PATENT DOCUMENTS

| | | |
|---|---|---|
| CN | 101385714 A | 3/2009 |
| CN | 101530390 A | 9/2009 |
| CN | 102048696 A | 5/2011 |
| CN | 102639129 A | 8/2012 |
| CN | 103551090 A * | 2/2014 |
| CN | 103551090 A | 2/2014 |
| CN | 104837482 A | 8/2015 |
| JP | 2009-533341 A | 9/2009 |
| JP | 2013-87096 A | 5/2013 |
| RU | 2480203 C2 | 10/2012 |
| WO | 2007/123790 A1 | 11/2007 |
| WO | 2014/140268 A1 | 9/2014 |

OTHER PUBLICATIONS

Kabara, Jon J., et al. "Fatty acids and derivatives as antimicrobial agents." Antimicrobial agents and chemotherapy 2.1 (1972): 23-28.*
Fu, Xiaowei, et al. "Enhancement of antimicrobial activities by the food-grade monolaurin microemulsion system." Journal of food process engineering 32.1 (2009): 104-111.*
Petra, Ševčíková, et al. "Formulation, antibacterial activity, and cytotoxicity of 1-monoacylglycerol microemulsions." European Journal of Lipid Science and Technology 116.4 (2014): 448-457.*
Zhang, Hui, et al. "Antimicrobial activity of a food-grade fully dilutable microemulsion against *Escherichia coli* and *Staphylococcus aureus*." International journal of food microbiology 135.3 (2009): 211-215.*
English translation of First Office Action corresponding to RU 2018109992 dated Nov. 14, 2019; 5 pages.
Extended European Search Report corresponding to EP 16845742.2 dated Jun. 7, 2019; 14 pages.
Examination Report corresponding to IN 201827014536 Date of Dispatch/Email: Mar. 9, 2020; 7 pages.
Bothiraja, Chellampillai et al., "Development of plumbagin-loaded phospholipid-Tween® 80 mixed micelles: formulation, optimization, effect on breast cancer cells and human blood/serum compatibility testing," *Ther. Deliv.* (2013) 4(10):1247-1259.
Database WPI Week 201424 2014 Thomson Scientific, London, GB; AN 2014-F75730 XP002791469.
Desbois, Andrew et al., "Antibacterial free fatty acids: activities, mechanisms of action and biotechnological potential," *Applied Microbiology and Biotechnology*, Springer, Berlin, DE (Dec. 3, 2009) 85(6): 1629-1642.

(Continued)

*Primary Examiner* — Bethany P Barham
*Assistant Examiner* — Peter Anthopolos
(74) *Attorney, Agent, or Firm* — Mintz Levin Cohn Ferris Glovsky and Popeo PC

(57) ABSTRACT

Non-vesicular nanoparticles which have antibacterial activity and are made from a C8-C28 fatty acid or a derivative thereof, a surfactant and an optional lipid.

8 Claims, 17 Drawing Sheets

(56) References Cited

OTHER PUBLICATIONS

Fu, Xiaowei et al., "Enhancement of Antimicrobial Activities by the Food-Grade Monolaurin Microemulsion System," *Journal of Food Process Engineering* (Feb. 2009) 32(1):104-111.
Obonyo, Marygorret et al., "Antibacterial Activities of Lipsomal Linolenic Acids against Antibiotic-Resistant *Helicobacter pylori*," *Molecular Pharmaceutics* (Jul. 24, 2012) 9:2677-2685.
Pohl, Carolina H. et al., "Antifungal free fatty acids: A Review," *Science Against Microbial Pathogens Communicating Current Research and Technological Advances* (2011; Retrieved from the Internet URL:http://www.formatex.info/microbiology3/book/61-71.pdf [retrieved on Nov. 22, 2012].
Sonawane, Sandeep J. et al., "Transforming linoleic acid into nanoemulsion for enhanced activity against methicillin susceptible and resistant *Staphylococcus aureus*," *RSC Advances* (Oct. 19, 2015) 5(110):90482-90492.
Taylor, Eric N. et al., "Multi-scale strategy to eradicate Pseudomonas aeruginosa on surfaces using solid Tipid nanoparticles loaded with free fatty acids," *Nanoscale* (Jan. 2014) 5(2):825-832.
Umerska, Anita et al., "Antibacterial action of lipid nanocapsules containing fatty acids or monoglycerides as co-surfactants," *European Journal of Pharmaceutics and Biopharmaceutics* (Sep. 3, 2016) 108:100-110.
Yang, Darren et al., "The antimicrobial activity of liposomal lauric acids against *Propionibacterium acnes*," *Biomaterials* (Available online Aug. 8, 2009) 30:6035-6040.
English translation of Second Office Action corresponding to RU 2018109992 dated Apr. 27, 2020; 4 pages.
First Office Action corresponding to BR112018005268-0 dated Sep. 10, 2020.
English translation of First Office Action corresponding to JP 2018-533994; 7 pages.
Zhang, H. et al., "Development and antifungal evaluation of a food-grade U-type microemulsion," *Journal of Applied Microbiology* (2008; accepted Mar. 2, 2008) 993-1001.
Zhang, Hui et al., "Antimicrobial activity of a food-grade fully dilutable microemulsion against *Escherichia coli* and *Staphylococcus aureus*," *International Journal of Food Microbiology* (2009; accepted Aug. 8, 2009) 135:211-215.
Zhang, Hui et al., "Structure-Activity Relationship of a U-Type Antimicrobial Microemulsion System," *PLOS One* (Oct. 18, 2013) 8(10) e76245; 6 pages.
English Translation of the International Search Report corresponding to PCT/CN2016/099136 dated Jan. 23, 2017, 3 pages.
Ma, Wanshun et al., "Progress of Antibacterial Mechanisms Study on Nanoparticles," Biophysics Reports (Aug. 31, 2010); 26(8) :638-648.

* cited by examiner (A)

(B)

(C)

(D)

(a)

(b)

(a)

(b)

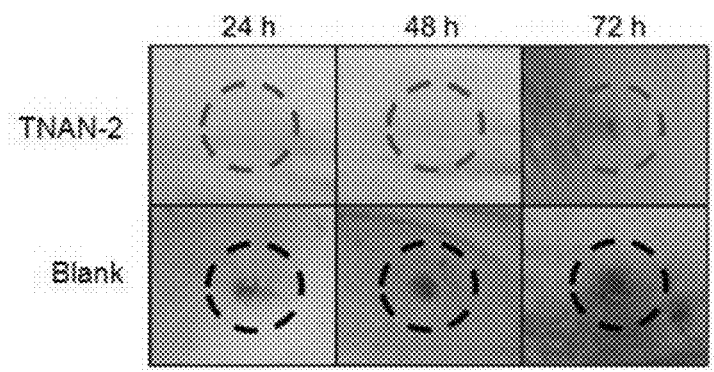
Fig. 25
Fig. 26
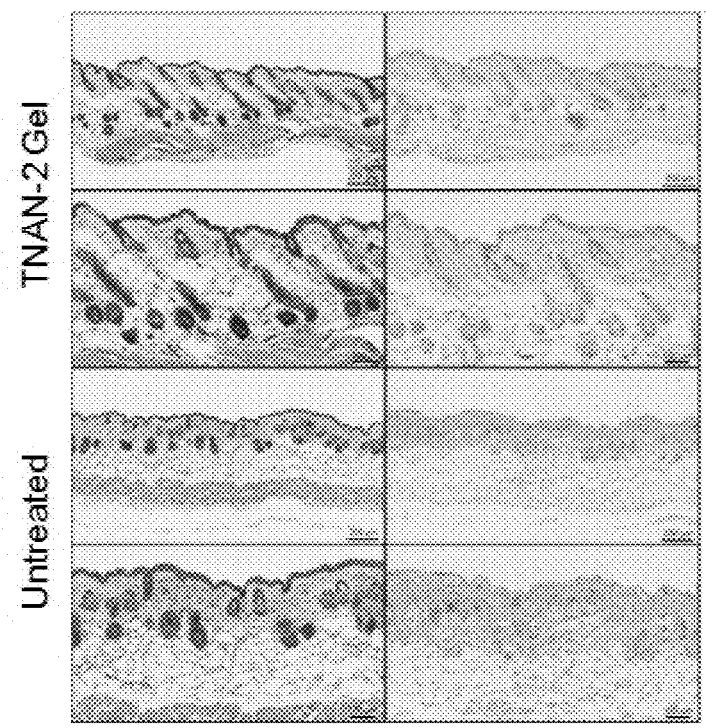
Fig. 27

| Size (d.nm) | Number (%) |
|---|---|
| 4.849 | 0.000 |
| 5.615 | 5.762 |
| 6.503 | 19.116 |
| 7.531 | 26.680 |
| 8.721 | 22.344 |
| 10.100 | 13.883 |
| 11.696 | 7.110 |
| 13.545 | 3.166 |
| 15.686 | 1.262 |
| 18.166 | 0.458 |
| 21.037 | 0.153 |
| 24.363 | 0.047 |
| 28.214 | 0.014 |
| 32.674 | 0.004 |
| 37.840 | 0.001 |
| 43.821 | 0.000 |

| Size (d.nm) | Number (%) |
|---|---|
| 3.615 | 0.000 |
| 4.187 | 0.200 |
| 4.849 | 3.000 |
| 5.615 | 7.800 |
| 6.503 | 13.000 |
| 7.531 | 16.800 |
| 8.721 | 18.000 |
| 10.100 | 16.400 |
| 11.700 | 12.600 |
| 13.540 | 7.800 |
| 15.690 | 3.500 |
| 18.170 | 0.800 |
| 21.040 | 0.000 | ically, the present invention relates to a highly stable, non-vesicular nanoparticle and the use of such a nanoparticle in treating microbial infections.

HIGHLY STABLE NON-VESICULAR NANOPARTICLES AND APPLICATION THEREOF IN TREATING MICROBIAL INFECTION

TECHNICAL FIELD

The present invention relates to the field of medicine. In particular, the present invention relates to a highly stable, non-vesicular nanoparticle and the use of such a nanoparticle in treating microbial infections.

BACKGROUND

Microorganism is a collective term for all of tiny organisms which can not be easily observed with naked eyes, including a large group of organisms including bacteria, fungi, some small protists, microalgae, and viruses. They are small and closely related to human beings, covering a wide range of beneficial and harmful species, covering a wide range of fields such as food, medicine, industry and agriculture, and environmental protection.

One of the most important effects of microorganisms on humans is the spread of infectious diseases. Great progress has been achieved in the prevention and treatment of diseases, however new and re-occurred microbial infections constantly appeared. The pathogenesis of some microbial infections is not clear, resulting in the lack of effective treatments. However, the abuse of a large number of broad-spectrum antibiotics has caused a great pressure of choice, resulting in mutations of many strains, thereby leading to the emergence of drug resistance and new threats to human health. For example, Tuberculosis infection which used to be controlled, is prevalent in the world again due to the emergence of drug-resistant *Mycobacterium tuberculosis*.

For another example, staphylococci, especially *Staphylococcus aureus*, is one of the major causes of fatal nosocomial infections and community infections. In recent decades, *S. aureus* has experienced several generations of resistance to antibiotics and is now resistant to the entire beta-lactam antibiotics, including penicillins, cephalosporins and carbapenem antibiotics. *Staphylococcus aureus*, which is resistant to beta-lactam antibiotics, is also known as methicillin-resistant *Staphylococcus aureus* (MRSA), or superbugs. The growing prevalence of MRSA infections has led to the widespread use of vancomycin, one of the only antibiotics that remain effective against MRSA. However, vancomycin can only inhibit MRSA instead of eradicating them. In addition, the extensive use of vancomycin has led to the emergence of vancomycin-resistant *Staphylococcus aureus* since the late 1990s. All of these facts highlight the importance and urgency of developing new and effective methods for treating MRSA.

Recent studies on novel anti-MRSA drugs include the synthesis of new drugs based on existing antibiotics, the development of immunoglobulins for the target-clearance of MRSA toxins and the development of natural antibiotics such as cationic antimicrobial peptides, liposomes and other endogenous substances. Although these new synthetic drugs have yielded good clinical trial results, they have similar structure and antibacterial mechanisms to existing antibiotics and, as a result, MRSA will be resistant to synthetic drugs shortly after their have been widely clinically used. Passive neutralization of bacterial toxin factors by injecting anti-virus globulins and antibody fragments may be beneficial to improve acute infection, but this method does not inhibit or eradicate the bacteria themselves. And in the long run, it will still lead to recurrent infections.

Some microorganisms infect specific sites, thereby rendering the drug either inaccessible or ineffective. For example, *Helicobacter Pylori*, found in the stomach, is the most common bacterial pathogen in the world and infects more than half the world's population. Infections of *Helicobacter pylori* cause a variety of stomach diseases, including chronic gastritis, gastric ulcer and stomach cancer.

At present, a universal treatment plan for *H. pylori* infection in the world is triple therapy, that is, two antibiotics (clarithromycin+amoxicillin or metronidazole) in combination with a proton pump inhibitor. However, due to the rapid emergence of *H. pylori* strains resistant to existing antibiotics, the eradication rates of current treating regimens have been rapidly reduced. For example, the clearance of triple therapy for *H. pylori* has dropped to 60 to 75%. The main reason is that *H. pylori* strains are resistant to these antibiotics. In particular, the resistance of key component of triple therapy, metronidazole, is more obvious. In developed countries, such resistance is 40% and in developing countries, 90%. Regarding these emerging resistances, different types of antibiotics have been developed, but the results are not satisfactory. In addition, the newly developed antibiotics and their applications are also limited by poor compliance of patients, high side effects, and the high cost of antibiotic treatment. Obviously, new treating solutions in clinic with excellent therapeutic effects and less side effects are needed.

Still other microbial infections, while generally do not cause serious, for example, fatal consequences, can seriously affect people's quality of life. For example, acne infection is a common skin condition and 80% of people have or have been affected by it. The main cause of acne is the excessive secretion of sebum leading to the clogging of hair follicles, resulting in a localized hypoxic or anaerobic environment, which stimulates rapid propagation of *Propionibacterium acnes*. *Propionibacterium acnes* is a Gram-positive anaerobic bacterium that is closely related to acne infections. Propagation of *P. acnes* causes rupture of the hair follicle wall so that host immune cells react to invading bacteria, leading to inflammatory acne. Serious inflammation of acne lesions can cause pigmentation and permanent skin scars, giving people embarrassment, stress and inferiority, thus affecting their mental health and mental development.

A number of antimicrobial agents have been developed and approved for treating acne, including adapalene, tazarotene, erythromycin, clindamycin, benzoyl peroxide (BPO), and other antibiotics. Although these antibiotics exhibit significant anti-acne effects, these drugs often have serious side effects. For example, BPO is one of the most commonly used skin remedies for acne; however, it causes a high incidence of erythema, scaling, burning of skin and whitening of hair. Although oral antibiotics are very effective, they are often accompanied by risks of damaging the intestinal flora and inducing resistant *P. acnes*. For example, isotretinoin is tretinoin derived from vitamin A for treating severe acne, and its use is strictly regulated. Most patients with acne can not use this drug due to its strong teratogenic effects. Therefore, new anti-acne drugs not only have good therapeutic effects, but also have very little toxic side effects and do not induce drug-resistant strains.

In addition to bacteria, fungi are also a group of microorganisms that seriously threaten human health. According to the site of the human body for fungal invasion, fungal infectious diseases are divided into four categories: superficial mycosis, dermatophytosis, subcutaneous tissue fungal disease and systemic fungal disease; the former two are known as superficial fungal diseases, and the latter two are known as deep fungal diseases.

At present, with the bone marrow and organ transplantation, chemotherapy of the tumor, long-term application of glucocorticoid and the widespread use of broad-spectrum antibiotics, the incidence of invasive fungal infections is increasing year by year, new pathogens continuously appear and the condition is worsening. Deep mycosis is the most damagerous in fungal infections and is also one of the nosocomial infections. Its clinical symptoms and signs are nonspecific. Deep mycosis is characterized in lack of effective diagnostic tools, rapid course of progression, poor prognosis, and more frequent use of prophylactic and empirical treatments. Currently, the clinical antifungal drugs can be divided into four categories: azoles, polyenes, acrylamines, flucytosine, etc., in which azoles are most widely used. There are limitations, such as narrow antibacterial spectrum, and high side effects, in the existing antifungal drugs, thereby limiting their clinical use. At the same time, with the extensive use of anti-fungal drugs, resistance rate of fungi continually increase, thus affecting the therapeutic effects of the drugs.

In the past decades, the application of nanotechnology in pharmacology has been widely explored. By physical coating or chemical binding, a drug can be loaded into nanoparticles, thereby significantly increasing the kinetic and therapeutic indices of the drug compared with the drug in a free form. The advantages of these nanoparticle-based drug delivery systems are generally focused on improving the serum solubility of the drug, extending the systemic circulation of the drug, and the sustained, controlled release of the drug. Because most of the drugs in these nanoparticles are traditional antibiotics, resistant strains will still develop. Moreover, the preparation process of the used nanoparticles is complicated, costly and has limited stability, which seriously affects the practical application value of such drugs.

Therefore, there is a great need in the art for highly efficient novel therapeutic agents against microbial infections without inducing drug-resistant strains.

SUMMARY OF THE INVENTION

It is an object of the present invention to provide a highly efficient novel therapeutic drug against microbial infection without inducing drug-resistant strains.

In the first aspect, a non-vesicular nanoparticle is provided in the invention, consisting of a fatty acid or a derivative thereof, a surfactant, and optionally a lipid.

In a preferred embodiment, the fatty acid is a C8-C28, preferably C12-C24, most preferably C12-C18, saturated or unsaturated fatty acid; and the derivative of fatty acid is a mono-, di-, or tri-glycerides of C10-C14, preferably C11-C13 fatty acid.

In a preferred embodiment, the unsaturated fatty acid contains 1 to 6, preferably 1 to 4, for example 1, 2 or 3 unsaturated bonds, preferably double bonds.

In a preferred embodiment, the fatty acids include, but not limited to, palmitic, stearic, oleic, linolenic, linoleic, lauric, myristoleic, arachidonic, eicosapentaenoic acid (hereinafter referred to as EPA), docosahexaenoic acid (hereinafter referred to as DHA), caprylic acid, capric acid and nonanoic acid.

In a specific embodiment, the fatty acid is linolenic acid, lauric acid or myristoleic acid; and the derivative of fatty acid is lauric acid monoglyceride, diglyceride or triglyceride, preferably lauric acid monoglyceride.

In a preferred embodiment, the surfactant includes, but not limited to one or more selected from a group consisting of sodium stearate, 4-(5-dodecyl) benzene sulfonate, polyoxyethylene glycol, Polysorbate 20, polysorbate 40, sorbitol ester 60, polysorbate 80, poloxamer, polyethylene glycol octylphenyl ether and Triton X-100.

In a preferred embodiment, the lipid is phospholipid and/or cholesterol.

In a preferred embodiment, the phospholipids include, but are not limited to, one or more selected from a group consisting of: phosphatidylethanolamine, phosphatidylinositol, phosphatidylserine, phosphatidylcholine, dimyristoylcerophospholipid, dipalmitoyl phosphatidylcholine, palmitoyl phosphatidylglycerol, and dioleyl phosphatidylethanolamine.

In a preferred embodiment, the mass ratio of the lipid to the surfactant is 10~0:1; preferably 5~0:1; more preferably 2.5~0:1.

In a preferred embodiment, the concentration of the fatty acid or a derivative thereof is 0.001 to 5% w/v; preferably 0.1 to 5% w/v; more preferably 0.2 to 4% w/v; and more preferably 0.3 to 3% w/v.

In a specific embodiment, the particle size of nanoparticles is 1-90 nm; preferably 2-80 nm; more preferably 5-50 nm; more preferably 5-20 nm; and most preferably 5-15 nm.

In a preferred embodiment, the particle size of the prepared nanoparticles can be 1-30 nm; 10-40 nm; 20-50 nm; 30-60 nm; 40-70 nm; 50-80 nm; 60-90 nm; or, the particle size of nanoparticles can be 5-25 nm; 15-35 nm; 25-45 nm; 35-55 nm; 45-65 nm; 55-75 nm; 65-85 nm; or the particle size of the nanoparticles can be 10-30 nm; 20-40 nm; 30-50 nm; 40-60 nm; 50-70 nm; 60-80 nm; 70-90 nm.

In a particular embodiment, the polydispersity index of the nanoparticles is <0.3; preferably <0.2.

In a preferred embodiment, the particle size of the nanoparticles is in a narrower range, for example about 5-10 nm, about 15-25 nm, about 20-30 nm, about 40-50 nm, about 65-75 nm, about 80-90 nm, or about 100-110 nm.

In a specific embodiment, the stability of the non-vesicular nanoparticle is:

After storing at room temperature to 37° C. for 3 months, the change in "Minimum Inhibitory Concentration" and "Minimum Bactericidal Concentration" values of the nanoparticles is less than 20%; preferably less than 10% as compared with the freshly prepared nanoparticles; or, After storing at room temperature for 1.5 months, preferably 3 months, the change in particle size of the nanoparticles is less than 20%; preferably less than 15%; more preferably less than 10% as compared with freshly prepared nanoparticles.

In a particular embodiment, the nanoparticles are prepared by a method comprising:

1) suspending a surfactant and optional lipid in water;
2) stirring the resulting suspension from 1) until a homogeneous suspension is formed;
3) heating the resulting homogeneous suspension from 2) to a temperature above the melting point of the surfactant and optional lipid contained therein;
4) adding a fatty acid or a derivative thereof into the hot suspension obtained in 3) and stirring;
5) cooling and standing the resulting suspension from 4) to obtain a suspension of the non-vesicular nanoparticles of the present invention.

In a specific embodiment, the nanoparticles of the present invention are used for preparing an anti-microbial infection agent or for treating a microbial infection.

The microorganisms include: bacteria and fungi; the bacteria include: gram positive bacteria and gram negative bacteria; the gram positive bacteria include: *Staphylococcus*; preferably *Staphylococcus aureus*; more preferably methicillin-resistant *Staphylococcus aureus*; *Propionibacterium*; preferably *Propionibacterium freudennreichii, Propionibacterium acnes, Propionibacterium avidum, Propionibacterium granulosum*; more preferably *Propionibacterium acnes*; and The Gram-negative bacteria include: *Helicobacter Pylori, Pseudomonas aeruginosa*; preferably *Helicobacter pylori;*

The fungi include, but not limited to, *coccidioides, coccidioides, Dermatitis Blastomyces*, pigmented fungi, *Mycobacterium, Sporotrichosis, Trichophyton, Candida, Cryptococcus, Aspergillus, mucor*, Actinomycesbovis, *Nocardia*, etc.; preferably *Trichophyton* and *Aspergillus*; more preferably *Trichophyton rubrum, Aspergillus fumigatus, Candidia albicans*, Mycelium yellow ringworm; and most preferably *Trichophyton rubrum, Aspergillus fumigatus*.

In the second aspect, a method for preparing a non-vesicular nanoparticle of the first aspect of the invention is provided in the present invention, comprising following steps of:

1) suspending a surfactant and optional lipid in water;
2) stirring the resulting suspension from 1) until a homogeneous suspension is formed;
3) heating the resulting homogeneous suspension from 2) to a temperature above the melting point of the surfactant and optional lipid contained therein;
4) adding a fatty acid or a derivative thereof into the hot suspension obtained in 3) and stirring;
5) cooling and standing the resulting suspension from 4) to obtain the non-vesicular nanoparticle of any one of claims 1-5.

In a preferred embodiment, the melting point in the method is 20° C.-80° C., such as 20° C., 30° C., 40° C., 50° C., 60° C., 70° C., or 80° C.

In a preferred embodiment, the method may further comprise detecting the hydrodynamic size of the resulting nanoparticles.

In a preferred embodiment, the fatty acid is a C8-C28, preferably C12-C24, most preferably C12-C18, saturated or unsaturated fatty acid; and the derivative of fatty acid is a mono-, di-, or tri-glycerides of a C10-C14, preferably C11-C13 fatty acid.

In a preferred embodiment, the unsaturated fatty acid is a fatty acid containing one or more, preferably 1-4, double bonds.

In a preferred embodiment, the fatty acid includes, but not limited to, palmitic acid, stearic acid, oleic acid, linolenic acid, linoleic acid, lauric acid, myristoleic acid, arachidonic acid, EPA, DHA, caprylic acid, capric acid and nonanoic acid.

In a preferred embodiment, the surfactant includes, but not limited to one or more selected from a group consisting of sodium stearate, 4-(5-dodecyl) benzene sulfonate, polyoxyethylene glycol, polysorbate 20, polysorbate 40, polysorbate 60, polysorbate 80, poloxamer, polyethylene glycol octylphenyl ether and Triton X-100.

In a preferred embodiment, the lipid is phospholipid and/or cholesterol.

In a preferred embodiment, the phospholipids include, but not limited to, one or more selected from a group consisting of: phosphatidylethanolamine, phosphatidylinositol, phosphatidylserine, phosphatidylcholine, dimyristoylcerophospholipid, dipalmitoyl Phosphatidylcholine, palmitoyl phosphatidylglycerol, and dioleyl phosphatidylethanolamine.

In a preferred embodiment, the mass ratio of the lipid to the surfactant is 10~0:1; preferably 5~0:1; more preferably 2.5~0:1.

In a preferred embodiment, the concentration of the fatty acid is 0.001-5% w/v; preferably 0.1-5% w/v; more preferably 0.2-4% w/v; more preferably 0.3-3% w/v.

In a preferred embodiment, the particle size of prepared nanoparticles is 1-90 nm; preferably 2-80 nm; more preferably 5-50 nm; more preferably 5-20 nm; and most preferably 5-15 nm.

In a preferred embodiment, the particle size of the prepared nanoparticles can be 1-30 nm; 10-40 nm; 20-50 nm; 30-60 nm; 40-70 nm; 50-80 nm; 60-90 nm; or, the particle size of the nanoparticle can be 5-25 nm; 15-35 nm; 25-45 nm; 35-55 nm; 45-65 nm; 55-75 nm; 65-85 nm; or the particle size of the nanoparticle can be 10-30 nm; 20-40 nm; 30-50 nm; 40-60 nm; 50-70 nm; 60-80 nm; 70-90 nm.

In a preferred embodiment, the polydispersity index of the nanoparticles is <0.3; preferably <0.2.

In a preferred embodiment, the particle size of the nanoparticles is in a narrower range, for example about 5-10 nm, about 15-25 nm, about 20-30 nm, about 40-50 nm, about 65-75 nm, about 80-90 nm, or about 100-110 nm.

In a preferred embodiment, the stability of the non-vesicular nanoparticle is:

After storing at room temperature to 37° C. for 3 months, the change in "Minimum Inhibitory Concentration" and "Minimum Bactericidal Concentration" values of the nanoparticles is less than 20%; preferably less than 10% as compared with the freshly prepared nanoparticles; or, After storing at room temperature for 1.5 months, preferably 3 months, the change in particle size of the nanoparticles is less than 20%; preferably less than 15%; more preferably less than 10% as compared with freshly prepared nanoparticles.

In the third aspect, a pharmaceutical composition is provided in the invention, comprising the non-vesicular nanoparticle of the first aspect of the invention and, optionally, a pharmaceutically acceptable carrier.

In a preferred embodiment, a dosage form of the pharmaceutical composition includes, but not limited to, a dosage form suitable for systemic administration, or a dosage form for topical or topical administration;

Further the dosage form includes, but not limited to, a tablet, solution, suspension, capsule, granule, powder, injection, patche, spray, ointment, oil ointment, paste, gel, cream, drop, spray, lotion;

And dosage form for topical or topical administration is preferred, including but not limited to: a patche, spray, ointment, oil ointment, paste, gel, cream, drop, spray, lotion.

In a preferred embodiment, the pharmaceutically acceptable carrier includes, but not limited to, water; saline; a binding agent (e.g., polyvinylpyrrolidone or hydroxypropylmethylcellulose); a filler (e.g., lactose and other saccharides, gelatin or calcium sulfate), a lubricant (e.g., starch, polyethylene glycol or sodium acetate), a disintegrant (e.g., starch or sodium starch glycolate), and a wetting agent (e.g., sodium lauryl sulphate).

In a preferred embodiment, the pharmaceutical composition may further contain a penetration enhancer; the penetration enhancer includes, but not limited to, a surfactant (e.g., sodium lauryl sulfate, polyoxyethylene-9-ether and polyoxyethylene-20-hexadecyl ether); a bile salt (e.g., cholic acid, dehydrocholic acid and deoxycholic acid); a chelating agent (e.g., disodium ethylenediaminetetraacetate, citric acid and salicylate); and a non-chelating non-surfactant (e.g., unsaturated cyclic urea).

In a specific embodiment, the pharmaceutical composition may further comprise other antibiotics.

In a preferred embodiment, the antibiotic is an antibiotic against infections caused by *Staphylococcus*, preferably *Staphylococcus aureus*, more preferably Methicillin-resistant *Staphylococcus aureus*, including but not limited to: vancomycin, cephalosporin, linezolid, teicoplanin, abamectin, quinuclidine, dalfopristin, quinuptin, clindamycin, daptomycin, Rifampin, tiraceans, tetracyclines, such as tigecycline and the like; or, The antibiotic is an antibiotic for treating infection caused by *P. acnes*, including but not limited to adapalene, tazarotene, erythromycin, clindamycin, azithromycin, minocycline, roxithromycin, Tretinoin and benzoyl peroxide (BPO);

Alternatively, the antibiotic is an antibiotic for treating infection caused by *Helicobacter Pylori*, including but not limited to: clarithromycin, amoxicillin, metronidazole, tinidazole, furazolidone, tetracycline and the like;

Alternatively, the antibiotic is an anti-fungal antibiotic, including but not limited to clotrimazole, nystatin, fluconazole, ketoconazole, itraconazole, miconazole, terbinafine, Amorolfine, amphotericin B, griseofulvin, ciclopirox olamine, caspofungin and the like;

Alternatively, the antibiotics may be quinolones, β-lactams, macrolides, aminoglycosides, amidols, nitroimidazoles and the like.

In a particular embodiment, the pharmaceutical composition is an aqueous pharmaceutical composition.

In the fourth aspect, the invention provides the use of the nanoparticle of the first aspect of the invention or the pharmaceutical composition of the third aspect of the invention in the preparation of an antimicrobial agent.

In a particular embodiment, the microorganisms include: bacteria, fungi.

In a particular embodiment, the bacteria include: Gram-positive bacteria and Gram-negative bacteria.

In a particular embodiment, the Gram-positive bacteria include: *Staphylococcus*; preferably *Staphylococcus aureus*; more preferably methicillin-resistant *Staphylococcus aureus*, *Propionibacterium*; preferably *Propionibacterium freudennreichii, Propionibacterium acnes, Propionibacterium avidum, Propionibacterium granulosum*; more preferably *Propionibacterium acnes*; and The Gram-negative bacteria include: *Helicobacter Pylori, Pseudomonas aeruginosa*; preferably *Helicobacter pylori*.

In particular embodiments, the fungi include, but not limited to, *coccidioides, coccidioides, Dermatitis Blastomyces*, pigmented fungi, *Mycobacterium*, Sporotrichosis, *Trichophyton, Candida, Cryptococcus, Aspergillus*, mucor, Actinomycesbovis, *Nocardia*, etc.; preferably *Trichophyton* and *Aspergillus*; more preferably *Trichophyton rubrum, Aspergillus fumigatus, Candidia albicans*, Mycelium yellow ringworm; and most preferably *Trichophyton rubrum, Aspergillus fumigatus*.

In the fifth aspect, a treating method is provided in the invention, comprising administering the nanoparticles of the first aspect of the invention to a subject for treating microbial infections.

A treating method is further provided in the present invention, comprising administering the nanoparticles of the first aspect of the invention to a subject in combination with another antibiotic for treating microbial infections.

In a preferred embodiment, the antibiotic is an antibiotic against infections caused by *Staphylococcus*, preferably *Staphylococcus aureus*, more preferably Methicillin-resistant *Staphylococcus aureus*, including but not limited to: vancomycin, cephalosporin, linezolid, teicoplanin, abamectin, quinuclidine, dalfopristin, quinuptin, clindamycin, daptomycin, Rifampin, tiraceans, tetracyclines, such as tigecycline and the like; or, The antibiotic is an antibiotic for treating infection caused by *P. acnes*, including but not limited to adapalene, tazarotene, erythromycin, clindamycin, azithromycin, minocycline, roxithromycin, Tretinoin and benzoyl peroxide (BPO);

the antibiotic is an antibiotic for treating infection caused by *Helicobacter Pylori*, including but not limited to: clarithromycin, amoxicillin, metronidazole, tinidazole, furazolidone, tetracycline and the like;

The antibiotic is an antibiotic treating infections caused by *Pseudomonas aeruginosa* and includes, but not limited to, piperacillin, azlocillin, ceftriaxone, cefoperazone sulbactam, amikacin, gentamicin, Polymyxin B and the like;

the antibiotic is an anti-fungal antibiotic, including but not limited to clotrimazole, nystatin, fluconazole, ketoconazole, itraconazole, miconazole, terbinafine, Amorolfine, amphotericin B, griseofulvin, ciclopirox olamine, caspofungin and the like.

In a preferred embodiment, the nanoparticles and other antibiotics are administered at the same or different administration times using the same or different routes of administration.

It should be understood that in the present invention, the technical features specifically mentioned above and below (such as in the Examples) can be combined with each other, thereby constituting a new or preferred technical solution which needs not be individually described.

DESCRIPTION OF DRAWINGS

FIG. 25 shows in vivo antibacterial activity of the nanoparticles of the invention containing 1% w/v linolenic acid in mice subcutaneously infected with MRSA 252. During the experiment, mice were subcutaneously injected with 1*10⁶ CFU of MRSA252 and then injected with the nanoparticles of the invention at the same site after 20 minutes. The picture shows conditions of the injured sites at 24, 48, and 72 hours after MRSA injection.

FIG. 26 shows 7-day in vivo toxicity study of topical gel dosage form of the nanoparticles of the present invention containing 1% w/v linolenic acid. It was shown by Draize Scoring System that using the dosage form of the nanoparticles of the present invention did not produce significant edema or erythema. Images are representative for 5 mice in each group.

FIG. 27 shows the evaluation of H & E (left panel) and TUNEL (right panel) to assess in vivo toxicity of the nanoparticles of the invention containing 1% w/v linolenic acid. Blank PBS gel was used as a negative control. The dosage forms of nanoparticle of the invention produced no inflammation and no significant cell death. Images are representative of 5 mice in each group.

MODE FOR CARRYING OUT THE INVENTION

Figure 1:
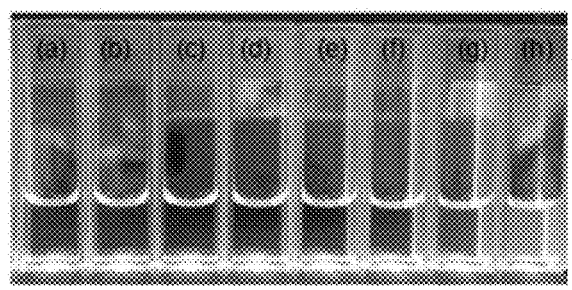
FIG. 1 is photographs of a set of nanoparticles of the present invention; wherein: Panel A shows linolenic acid concentrations ranging from (a) 0.1% w/v to (h) 4% w/v (% w/v=wt %); Panel B shows lauric acid concentrations ranging from (a) 0.1% w/v to (f) 5% w/v; Panel C shows that myristoleic acid concentrations from (a) 0.1% w/v to (h) 4% w/v; Panel D shows lauric acid monoglyceride concentrations from 0.1% w/w to 0.8% w/w. Ideal nanoparticle dosage forms can be determined based on physical properties, such as aggregation degree and clarity of these samples.
Figure 1:
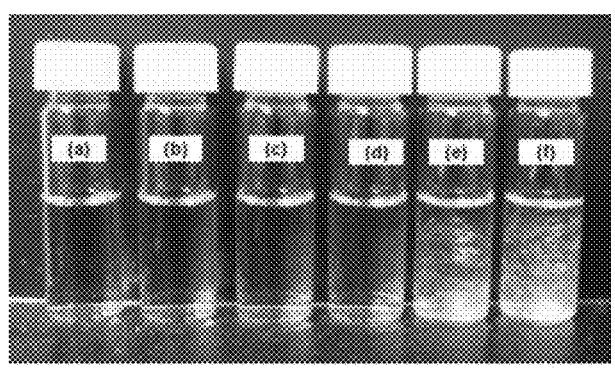
Figure 1:
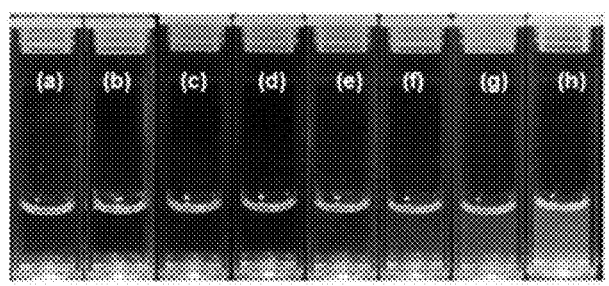
Figure 1:
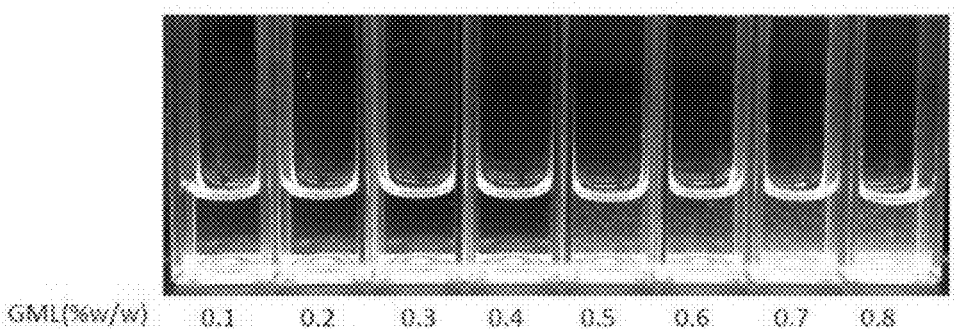

After extensive and intensive research, the inventors unexpectedly discovered that non-vesicular nanoparticles (nanoparticle in micellar structure) made of fatty acid or a derivative thereof (for example, fatty acid glyceride), surfactant, and optional lipid not only possesses significant antibacterial activity but also excellent stability, and the non-vesicular nanoparticle of the present invention can be used as an excellent antibacterial drug without inducing drug-resistant strains. Based on the above findings, the present invention has been completed.

Fatty Acid

The term "fatty acid" as used herein has the meaning as commonly understood by a skilled person; that is, the fatty acid is an amphiphilic molecule consisting of a hydrophobic hydrocarbon chain and a hydrophilic carboxylic acid head group.

It is known to a skilled person that certain fatty acids possess certain antimicrobial ability, however due to specific nature of fatty acids themselves, such as insolubility in water, fatty acids can not be directly used as a medicament or organic solvents are needed for administration. For example, lauric acid, a free fatty acid present in human sebum, is more potent than benzoyl peroxide in antibacterial activity. However, due to its poor water solubility, lauric acid must be dissolved in a solvent such as dimethyl sulfoxide (DMSO) to form an external dosage form, whereas DMSO exhibits irritating and toxic side effects. Therefore, in the prior art, there are many limitations on the use of fatty acids as drugs.

Compared with the prior art, in the present invention, fatty acids can be delivered without using organic solvents against antimicrobial infections, thereby breaking through limitations of fatty acids in pharmaceutical applications and utilizing a number of fatty acids which are difficult to be used in prior art as medicaments. Fatty acids suitable for using in the present invention are C8-C28, preferably C12-C24, more preferably C12-C18, saturated or unsaturated fatty acids. In a preferred embodiment, the unsaturated fatty acid contains 1 to 6, preferably 1 to 4, for example 1, 2, 3 or 4, unsaturated bonds, preferably double bonds. In a particular embodiment, fatty acids suitable for using in the present invention include, but not limited to, palmitic, stearic, oleic, linolenic, linoleic, lauric, myristoleic, arachidonic, EPA, DHA, caprylic acid, capric acid and nonanoic acid. In a further preferred embodiment, fatty acids suitable for using in the present invention include, but not limited to, linolenic acid, lauric acid, myristoleic acid.

In view of the teachings of the present invention, a skilled person will appreciate that "fatty acids" described herein include derivatives thereof, i.e., the "fatty acids" described herein include three forms (acid, salt and ester) of fatty acids. In a specific embodiment, the fatty acid derivative in the non-vesicular nanoparticle of the present invention is a monoglyceride, diglyceride or triglyceride of a C10-C14, preferably C11-C13 fatty acid. In a specific embodiment, the fatty acid is a saturated fatty acid, preferably lauric acid. In a preferred embodiment, the fatty acid derivative is lauric acid monoglyceride. The term "lauric acid monoglyceride" as used herein includes isomers of lauric acid monoglyceride wherein glycerol hydroxyl is in different R, S configurations, 1-hydroxy substituted lauric acid monoglyceride, 2-hydroxy substituted lauric acid monoglyceride, and any mixture thereof.

Non-Vesicular Nanoparticle

The terms "nanoparticle", "nanoparticle of the present invention", "non-vesicular nanoparticle" and "non-vesicular nanoparticle of the present invention" as used herein have the same meaning, and refer to nanoparticles of no vesicular form. In particular, the non-vesicular nanoparticle of the present invention is defined relative to other nanoparticles with a cavity structure, that is, the non-vesicular nanoparticle of the present invention is a nanoparticle in which no cavity is present. In addition, based on the preparation method described below for the nanoparticle of the present invention, a skilled person can understand that the nanoparticle of the present invention is a system of nanoparticles, that is, nanoparticles in an aqueous system or an aqueous system containing nanoparticles. In other words, the nanoparticle described in the present invention is an aqueous system of nanoparticles, that is, a nanoparticle system without organic solvent.

Figure 35:
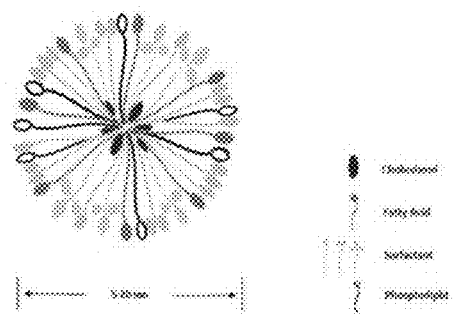
FIG. 35 shows a schematic diagram of the structure of nanoparticles of the present invention.

The nanoparticles of the present invention can be used to deliver natural antibacterial substances such as fatty acids and derivatives thereof (such as lauric acid monoglyceride) to sites infected by microorganisms, such as bacteria or fungi, while avoiding using solvents such as DMSO. The non-vesicular nanoparticle provided in the present invention consists of a fatty acid or a derivative thereof, a surfactant, and optionally, a lipid. The molecules of these components have a hydrophilic portion and a hydrophobic portion consisting of an elongated hydrocarbon chain. For example, a fatty acid is an amphipathic molecule consisting of a hydrophobic hydrocarbon chain and a hydrophilic carboxylic acid head group. As another example, a fatty acid glyceride, such as lauric acid monoglyceride, consists of a hydrophobic hydrocarbon chain and a hydrophilic glycerol head group. In such structure, fatty acids or fatty acid esters are allowed to be incorporated into nanomicelles, nanoparticles with an amphipathic environment. In the presence of water, the hydrophilic portion and surfactant are arranged to form a water-facing surface, while the hydrophobic portions are arranged to form a core diviated from the water, thereby forming nanostructure of micelles (as shown in FIG. 35).

The lipids contained in the non-vesicular nanoparticle of the present invention may be phospholipids and/or cholesterol. In a particular embodiment, the lipid is a phospholipid, including but not limited to one or more selected from: phosphatidylethanolamine, phosphatidylinositol, phosphatidylserine, phosphatidylcholine, dimyristoylcerophospholipid, dipalmitoylphosphatidylcholine, palmitoylphosphatidylglycerol, and dioleylphosphatidylethanolamine.

Surfactants suitably to be used in the present invention include, but not limited to, one or more selected from: sodium stearate, 4-(5-dodecyl) benzene sulfonate, polyoxyethylene glycol, polysorbate 20, polysorbate 40, polysorbate 60, polysorbate 80, poloxamer, polyethylene glycol octylphenyl ether and Triton X-100.

In a specific embodiment, the excipient material for the nanoparticle of the present invention may include phosphatidylcholine, cholesterol, lecithin, polysorbate 20, polysorbate 80 and sodium dodecyl sulfate.

In the non-vesicular nanoparticle of the present invention, the ratio of lipid to surfactant may be 10~0:1; preferably 5~0:1; and more preferably 2.5~0:1.

The non-vesicular nanoparticle of the present invention contains an appropriate amount of fatty acid or a derivative thereof. In a particular embodiment, the fatty acid or a derivative thereof is present at a concentration of 0.001 to 5% w/v; preferably 0.1 to 5% w/v; more preferably 0.2 to 4% w/v; more preferably 0.3 to 3% w/v. In a preferred embodiment, the nanoparticle of the invention may comprise 1.0% w/v linolenic acid or lauric acid, or 0.3% w/v myristoleic acid, or 0.4% w/v lauric acid monoglyceride. A skilled person will appreciate that the concentration of a fatty acid or derivative thereof described herein refers to the concentration of the fatty acid or derivative thereof in a system comprising nanoparticles of the invention, in particular an aqueous system, for example, an aqueous suspension.

The non-vesicular nanoparticle of the present invention possesses a series of physical and chemical characteristics, such as the diameter of nanoparticles and the concentration of linolenic acid or lauric acid glyceride (i.e., mass percentage of linolenic acid or lauric acid glyceride in the suspension of nanoparticles). The diameter of the nanoparticles can be measured using dynamic light scattering. The average diameter of non-vesicular nanoparticles of the present invention is about 1 to 90 nm; preferably 2 to 80 nm; more preferably 5 to 50 nm; more preferably 5 to 20 nm; most preferably 5 to 15 nm.

In other embodiments, the particle size of the nanoparticles may be 1-30 nm; 10-40 nm; 20-50 nm; 30-60 nm; 40-70 nm; 50-80 nm; 60-90 nm; alternatively, the particle size of the nanoparticles may be 5-25 nm; 15-35 nm; 25-45 nm; 35-55 nm; 45-65 nm; 55-75 nm; 65-85 nm; alternatively, the particle size of the nanoparticles may be 10-30 nm; 20-40 nm; 30-50 nm; 40-60 nm; 50-70 nm; 60-80 nm; 70-90 nm.

The non-vesicular nanoparticles of the present invention exhibit a uniform particle size distribution with a polydispersity coefficient of <0.3; preferably <0.2. In a preferred embodiment, the particle size of the nanoparticles is in a narrower range, for example about 5-10 nm, about 15-25 nm, about 20-30 nm, about 40-50 nm, about 65-75 nm, about 80-90 nm, or about 100-110 nm.

The non-vesicular nanoparticles of the present invention exhibit excellent stability. In a specific embodiment, the change in "minimum inhibitory concentration" and "minimum bactericidal concentration" values for the nanoparticles of the invention is less than 20%, preferably less than 10%, compared with that of freshly prepared nanoparticles after storing at various temperatures for 3 months. In another embodiment, the change in the particle size of the nanoparticles of the present invention is less than 20%, preferably less than 15%, more preferably less than 10%, after storing at room temperature for 1.5 months, preferably 3 months, compared with that of freshly prepared nanoparticles. The term "room temperature" as used herein has the meaning as commonly understood by a skill person and generally refers to 25° C.±5° C., or 25° C.±3° C., or 25° C.±1° C.

The non-vesicular nanoparticles of the present invention exhibit excellent antimicrobial activity. In a specific embodiment, the nanoparticles of the invention are capable of inhibiting or killing bacteria or fungi.

In a particular embodiment, the bacteria include, but not limited to: Gram-positive bacteria, Gram-negative bacteria; the Gram-positive bacteria include, but are not limited to: *Staphylococcus*; preferably *Staphylococcus aureus*; more preferably methicillin-resistant *Staphylococcus aureus, Propionibacterium*; preferably *Propionibacterium freudennreichii, Propionibacterium acnes, Propionibacterium avidum, Propionibacterium granulosum*; more preferably *Propionibacterium acnes;*

The Gram-negative bacteria include, but are not limited to: *Helicobacter Pylori, Pseudomonas aeruginosa;*

In another specific embodiment, the fungi include, but are not limited to: *coccidioides, coccidioides, Dermatitis Blastomyces*, pigmented fungi, *Mycobacterium, Sporotrichosis, Trichophyton, Candida, Cryptococcus, Aspergillus, mucor, Actinomycesbovis, Nocardia*, etc.; preferably *Trichophyton* and *Aspergillus*; more preferably *Candidia albicans, Trichophyton rubrum, Aspergillus fumigatus*, Mycelium yellow ringworm; and most preferably *Trichophyton rubrum, Aspergillus fumigatus*.

In a specific embodiment, the nanoparticles of the present invention exhibit a minimum inhibitory concentration (MIC) of 0.1% w/v and a minimum bactericidal concentration (MBC) of 0.2% w/v against $1\times10^6$ CFU of MRSA; in another specific embodiment, the nanoparticles of the present invention exhibit a minimum inhibitory concentration (MIC) of 0.0125% w/v and a minimum bactericidal concentration (MBC) of 0.02% w/v against *P. acnes*; in yet another specific embodiment, the nanoparticles of the present invention exhibit a minimum inhibitory concentration (MIC) of 0.0015% w/v and a minimum bactericidal concentration (MBC) of 0.0015% w/v against $5\times10^6$ CFU of *H. pylori*. In yet another specific embodiment, the non-vesicular nanoparticles of the present invention exhibit a MIC of 0.006% w/v against *Trichophyton rubrum* and a MIC of 0.1% w/v against *Aspergillus fumigatus*.

The ability of the nanoparticles of the present invention to inhibit microorganisms can be determined as follows. For example, the microorganism to be tested is in vitro co-incubated with the nanoparticles of the present invention in a medium or co-incubated in an animal model. The number of colonies of microorganisms (characterized as CFU) is then measured. As used herein, the term "inhibiting growth" refers to the ability of nanoparticles of the invention to inhibit increase in CFU when co-cultured with a microorganism. Therefore, when a certain microorganism is contacted with the nanoparticles of the present invention, its CFU won't change or decrease.

As used herein, the term "minimal inhibitory concentration" (MIC) refers to the minimum concentration of a drug, such as the nanoparticles of the present invention, that inhibits the growth of a microorganism, such as a bacterium (such as *Staphylococcus aureus*), or a fungi (such as *Trichophyton rubrum* and *Aspergillus fumigatus*). The MIC value can be determined by measuring the optical density of the microorganism after exposure to various concentrations of the nanoparticles of the present invention, especially whether $OD_{600}$ value or $OD_{450}$ value is changed. After a period of time, if $OD_{600}$ or $OD_{450}$ values do not rise, there was no increase in the number of bacteria or fungi in the culture broth.

As used herein, the term "minimum bactericidal concentration" (MBC) refers to the minimum concentration of a drug, such as the nanoparticles of the present invention, that is capable of killing microbial cells. MBC can be determined, for example, by counting colony growth on media co-cultured with different concentrations of the nanoparticles of the invention under certain conditions, for example at 37° C.

As used herein, the term "about" refers to the actual quoted number or value and to the upper and lower 10% of the quoted number or value.

Preparation Method for the Non-Vesicular Nanoparticles of the Present Invention

The non-vesicular nanoparticles of the present invention can be prepared by the following method, comprising following steps:

1) suspending a surfactant and optional lipid in water;
2) stirring the resulting suspension from 1) until a homogeneous suspension is formed;
3) heating the resulting homogeneous suspension from 2) to a temperature above the melting point of the surfactant and optional lipid contained therein;
4) adding a fatty acid or a derivative thereof into the hot suspension obtained in 3) and stirring;
5) cooling and placing the resulting suspension from 4) to obtain a suspension of the non-vesicular nanoparticles of the present invention.

In a specific embodiment, the melting point in the method is 20° C.-80° C., such as 20° C., 30° C., 40° C., 50° C., 60° C., 70° C. or 80° C.

In a further embodiment, the method may further comprise detecting the hydrodynamic size of the resulting nanoparticles.

Following parameters are to be considered when preparing the non-vesicular nanoparticles of the present invention, such as physico-chemical properties of raw materials and the material to be incorporated into the nanoparticles, the nature of the medium used to disperse the nanoparticles, the effective concentration of the loaded substance and potential toxicities thereof, processes involved in the application/delivery of nanoparticles, optimum size, polydispersity and shelf-life, batch reproducibility and the possibility for mass production of a safe and efficient product.

The nanoparticles of the present invention can not be spontaneously formed, which is formed when sufficient energy is provided to the fatty acids, such as linolenic acid and excipient material in water (e.g., by sonication, homogenization, shaking or heating).

The nanoparticles of the present invention can be prepared from various ingredients and by methods provided herein. Other preparation methods suitable for the nanoparticles of the present invention include agitation methods and heating methods, including high speed agitation. The advantages of such technique are simple equipment and easy production.

In some embodiments, the nanoparticles can be formed by high-pressure homogenization. High-pressure homogenization is widely used in various industries and is considered the most viable industrial application method. This technique involves preparation of solid lipid nanoparticles at a temperature above or below room temperature, and the particle size can be reduced by cavitation and vortexing. Liposomes and drugs can be thawed using hot high pressure homogenization and combined with an aqueous surfactant solution at the same temperature. The hot pre-emulsion is then processed in a temperature-controlled high-pressure homogenizer for typically up to 3 cycles at 500 bar. The obtained nanoemulsion recrystallized after cooling to room temperature to form solid liposome nanoparticles. Cold high pressure homogenization can be used to process hydrophilic drugs.

In addition to the above methods, any other methods for preparing solid liposome nanoparticles can be used to produce the nanoparticles of the present invention. Such methods include microemulsion methods, emulsion-solvent evaporation methods, emulsion solvent diffusion methods, solvent injection methods and invered-phase methods.

The nanoparticles obtained by the preparation method of the invention exhibit excellent stability in the structure and biological activity and the preparation method of the invention can has sufficiently utilize fatty acids or derivatives thereof.

Pharmaceutical Composition and Method for Using the Same

The nanoparticles of the present invention can be formulated into pharmaceutical compositions for use in humans and other mammals. When used, it may be mixed with other pharmaceutical carriers or diluents and the dosage and period of administration will be determined according to the nature and severity of the condition in a mammal. In general, the fatty acids or derivatives thereof in the nanoparticles of the present invention should be capable of achieving a pharmaceutically effective dosage; for example, a dosage which is effective to reduce the number of a microorganism, such as *Staphylococcus aureus* or fungi infecting a mammal, such as a human.

The formulations and methods of administration are well known to a skilled person. Usually, the course of treatment lasts from several days to several months until the condition is relieved, depending on the severity of the condition being treated and the response to the drug. The optimal dosage, method of administration and repetition rate will also be determinable by a skilled person. The optimal dosing amount can be adjusted according to the relative therapeutic efficacy of the nanoparticles of the present invention, and the using amount can generally be estimated from MIC and MBC values of in vitro and in vivo animal models. The frequency of dosing can be one or more times a day, twice a week, once a week or longer. After successful treatment, maintenance therapy should be performed to prevent the recurrence of infection.

As used herein, the terms "pharmaceutically acceptable carrier" and "excipient" have the same meaning, both of which refer to a pharmaceutically acceptable solvent, suspending agent, or any other pharmaceutically inert excipient used to deliver the nanoparticles of the present invention to a subject. The pharmaceutically acceptable carrier may be a liquid or solid, and the carrier should be selected according to the intended mode of administration so that when the nanoparticles of the present invention are used in combination with one or more therapeutic compounds or other pharmaceutical ingredients, the desired dosage, consistency and other drug delivery and chemical properties can be achieved.

Pharmaceutically acceptable carriers that do not adversely affect the nanoparticles of the present invention or destroy the nanostructures of the nanoparticles of the present invention include, but not limited to: water; saline; binding agents (e.g., polyvinylpyrrolidone or hydroxypropylmethylcellulose); fillers (e.g., lactose and other sugars, gelatin or calcium sulfate); lubricants (e.g., starch, polyethylene glycol or sodium acetate); disintegrants (e.g., starch or sodium starch glycolate); and wetting agents (e.g., sodium lauryl sulfate).

The nanoparticles of the present invention can be administered in a variety of ways, but usually topically administered. The nanoparticles of the present invention can be mixed with other molecules or used in combination with a mixture of other molecules, molecular structures or compound such as polyethylene glycol, petrolatum, or other topical formulations to facilitate the uptake, distribution and/or absorption of the drug. Dosage forms for topical administration may include sterile and non-sterile aqueous solutions, as well as non-aqueous solutions of common solvents such as ethanol or liquid or solid oleaginous solutions. Such solutions may also contain buffers, diluents and other suitable additives. Pharmaceutical dosage forms for topical administration include transdermal patches, ointments, lotions, creams, gels, drops, sprays, liquids and powders; with lotions, creams and gels being especially preferred. Conventional pharmaceutical carriers (aqueous, powdered, or oleaginous) may often be used, and other substances such as thickeners may also be used. In some cases, the nanoparticles of the invention may be suspended in a suspension of aqueous matrix, non-aqueous matrix or a mixed matrix. In the suspension, substances that increase the viscosity of the suspension, such as sodium carboxymethylcellulose, sorbitol, and/or dextran may also be contained. In the suspensions, stabilizers may also be contained.

In a preferred embodiment, the pharmaceutical composition of the present invention may also contain a penetration enhancer to enhance the effective penetration of the nanoparticles of the invention through mammalian skin. Penetration enhancers enhance both the ability of lipophilic and non-lipophilic drugs to cross the cell membrane. Penetration enhancers include, but not limited to: surfactants such as sodium dodecyl sulfate, polyoxyethylene-9-lauryl ether and polyoxyethylene-20-hexadecyl ether; bile acid salts, such as cholic acid, dehydrocholic acid and deoxycholic acid; chelating agents, such as disodium ethylenediaminetetraacetate, citric acid and salicylates; and non-chelating non-surfactants, such as unsaturated cyclic ureas.

In addition, in certain embodiments, the nanoparticles of the invention can be delivered by iontophoresis, for example, using a charged transdermal patch to "drive" the nanoparticles to arrive at the dermis.

The pharmaceutical composition of the present invention may also usually contain some other auxiliary pharmaceutical ingredients, including compatible pharmaceutically active materials, such as antipruritic agents, astringents, local anesthetics or anti-inflammatory agents, and other materials used to improve the physical properties of the dosage form (e.g., stains, preservatives, antioxidants, opacifiers, and stabilizers, etc.). Auxiliary agents, such as lubricants, preservatives, stabilizers, wetting agents, emulsifiers, salts for influencing osmotic pressure, buffers, colorants and aromatics can also be added. Of course, the addition of these auxiliary substances should not interfere with the activity and effects of the nanoparticles of the present invention. If necessary, formulations should be sterilized after prepared.

In view of the contents of the present invention and the teachings in the prior art, the pharmaceutical composition of the present invention can be prepared into a variety of dosage forms by a skilled person. In a specific embodiment, dosage forms of the pharmaceutical compositions of the present invention include, but not limited to, dosage forms suitable for systemic administration, or dosage forms for external or topical administration. Moreover, the dosage forms can include, but not limited to: tablets, solutions, suspensions, capsules, granules, powders, injections, patches, sprays, ointments, oil ointments, pastes, gels, creams, drops, sprays, lotions. In a specific embodiment, the pharmaceutical compositions of the present invention are externally or topically administered dosage forms including, but not limited to: patches, sprays, ointments, oil ointments, pastes, gels, creams, drops, sprays, lotions.

The pharmaceutical composition of the present invention can be used as an agent against microbial infection. The microorganism includes bacteria or fungi. For example, the bacteria include, but not limited to: Gram-positive bacteria, Gram-negative bacteria; the Gram-positive bacteria include, but not limited to: *Staphylococcus*; preferably *Staphylococcus aureus*; more preferably methicillin-resistant *Staphylococcus aureus*, or *Propionibacterium*; preferably *Propionibacterium freudennreichii, Propionibacterium acnes, Propionibacterium avidum, Propionibacterium granulosum*; more preferably *Propionibacterium acnes*; the Gram-negative bacteria include, but not limited to: *Helicobacter Pylori, Pseudomonas aeruginosa*; for another example, the fungi include, but not limited to: *coccidioides, coccidioides, Dermatitis Blastomyces*, pigmented fungi, *Mycobacterium, Sporotrichosis, Trichophyton, Candida, Cryptococcus, Aspergillus, mucor*, Actinomycesbovis, *Nocardia*, etc.; preferably *Trichophyton* and *Aspergillus*; more preferably *Candidia albicans, Trichophyton rubrum, Aspergillus fumigatus*, Mycelium yellow ringworm; and most preferably *Trichophyton rubrum, Aspergillus fumigatus*.

The pharmaceutical compositions of the present invention can treat infections caused by these microorganisms, in particular by reducing the amount of microorganisms such as staphylococci, propionibacteria, *Helicobacter pylori* or fungi that survive on the surface or in the body of a mammal (e.g., a human). These methods include applying the pharmaceutical composition of the present invention or the nanoparticles of the present invention to a lesion site of an infected mammal such as the skin to reduce the number of infected staphylococci or propionibacteria or fungal cells. The pharmaceutical composition or nanoparticles of the present invention may also alleviate the symptoms of infections caused by microorganisms, such as *Staphylococcus aureus* or *P. acnes* or fungal.

The pharmaceutical composition of the invention can also contain other conventional antibiotics, thereby being used in combination with other antibiotics so long as these other conventional antibiotics and the nanoparticles of the present invention do not adversely affect each other. Compared with using the conventional antibiotics alone, the combination of both can reduce the dosage of conventional antibiotics, reduce side effects and improve therapeutic effects. The additional antibiotic may be an antibiotic that treats a microbial infection identical with that treated with the nanoparticles of the present invention, thus increasing therapeutic effects; may also be an antibiotic that treats a microbial infection different from that treated with the nanoparticle of the invention, thereby treating different microbial infections or complicated microbial infections. The other conventional antibiotics may be quinolones, β-lactams, macrolides, aminoglycosides, amidols, nitroimidazoles and the like. For example, the other conventional antibiotics include, but not limited to: vancomycin, cephalosporin, linezolid, teicoplanin, abeaconazole, quinuclidine, dalfopristin, quinuptin, clindamycin, daptomycin, rifampicin, tivaradan, tetracyclines such as tigecycline and the like; or the other conventional antibiotics include, but not limited to, adapalene, tazarotene, erythromycin, clindamycin, azithromycin, minocycline, roxithromycin, isotretinoin, and benzoyl peroxide (BPO); or, the other conventional antibiotics include, but not limited to, amoxicillin, metronidazole, tinidazole, furazolidone, tetracycline and the like; or, the other conventional antibiotics are anti-fungal drugs including, but not limited to, clotrimazole, nystatin, fluconazole, Ketoconazole, itraconazole, miconazole, terbinafine, naftifine, amorolfine, amphotericin B, griseofulvin, ciclopirox olamine, caspofungin and the like.

In addition, those skilled in the art will appreciate that compared with the nanoparticles of the present invention, other antibiotics described above may be administered at the same time of administration and in the same route of administration; may be administered at the same time of administration and in a different route of administration; and alternatively, may be administered at a different time of administration and in the same route of administration. For example, the other antibiotics described above may be discretely present in the same pharmaceutical composition as the nanoparticles of the present invention (e.g., in a kit) and thus may be administered in the same or different route of administration and at the same or different time of administration.

In a preferred embodiment, the pharmaceutical composition of the present invention is an aqueous pharmaceutical composition, i.e., a pharmaceutical composition that is free of organic solvents. A skilled person can determine the concentration of the fatty acid or a derivative thereof in the pharmaceutical composition according to the teachings of the present invention and the actual desires.

Advantages of the Invention

1. The non-vesicular nanoparticles of the present invention exhibit significant antibacterial activity;
2. The ingredients in the non-vesicular nanoparticles of the present invention are selected from natural sources, showing high safety, non-toxic side effects;
3. The non-vesicular nanoparticles of the present invention exhibit excellent stability;
4. Organic solvents, such as DMSO are avoided to be used in the non-vesicular nanoparticles of the present invention for delivering the drug;
5. The preparation method for the non-vesicular nanoparticles of the present invention is simple, without using toxic and hazardous organic solvents such as chloroform, thereby reducing production costs and being environmentally friendly;
6. The particle size of the non-vesicular nanoparticles of the invention is small, thereby readily entering the tissue for bactericidal action;
7. The non-vesicular nanoparticles of the present invention exhibit small polydispersity, good homogeneity and stable bactericidal effects.

Unless defined otherwise, all technical and scientific terms used in the present invention are commonly understood by a skill person in the art to which this invention belongs. Although the present invention may be practiced using methods and materials similar or equivalent to those set forth herein, suitable methods and materials are set forth below. All publications, patent applications, patents, and other references mentioned herein are incorporated by reference in their entirety. In the event of any conflict between these publications, patent applications, patents and other references and the present application for a patent, the present specification (including definitions) shall control. In addition, materials, methods and examples in this application for a patent are for illustration only, and not intended to be limiting.

The present invention is further described below with reference to specific embodiments. It should be understood that these examples are only for illustrating the present invention and are not intended to limit the scope of the present invention. Experimental procedures in the following examples where no specific conditions are indicated are generally performed according to conventional conditions such as those described in Sambrook et al., Molecular Cloning: A Laboratory Manual (Cold Spring Harbor Laboratory Press, 2001), or conditions as recommended by the manufacturer. Unless otherwise indicated, percentages and parts are by weight.

EXAMPLE

Material and Method
Material:
Egg yolk lecithin (egg PC), cholesterol, C6-NBD phytosphingosine (C6NBD) and 1,2-dimyristoyl-sn-glycero-3-phosphoethanolamine-L-lysine Rhodamine B Acyl (DMPE-RhB) were purchased from Avanti Polar Lipids, Inc. (Alabaster, Ala.); linolenic acid, tryptic soy broth (TSB), phosphate buffered saline (PBS), trifluoroacetic acid (TFA), Acetonitrile and Sephadex G-75 were purchased from Sigma Aldrich (St. Louis, Mo.); and agar was purchased from BD (sparks, MD).

Lauric acid was purchased from Sigma Aldrich (St. Louis, Mo.). $KHCO_3$ was purchased from Fisher Scientific Division (Pittsburgh, Pa.). 3,4-difluorophenacyl bromide was purchased from Maybridge (Cambridge, England). Brinell medium (Lot 211088), aspirator (Lot 260683) and human agar (Lot 214010) were purchased from BD (Sparks, Md.). 1 liter of Brinell medium contains 10.0 g of Trypsin-digested casein, 10.0 g of pepsin-digested animal tissue, 1.0 g of glucose, 2.0 g of yeast extract, 5.0 g of sodium chloride and 0.1 g of sodium bisulfite. Defibrinated sheep blood (Lot Nos. R54016 and R54008) and Hematin chloride as well as Vitamin K solutions (Lot R450951) were purchased from Remel Corporation (Lenexa, Kans.). Intensive *Clostridium* medium (Lot OXCM0149B) was purchased from Oxoid Corporation (Hampshire, UK).

Myristolenic acid, tryptic soy broth (TSB), phosphate buffered saline (PBS), trifluoroacetic acid (TFA), acetonitrile and Sephadex G-75 were purchased from Sigma Aldrich (St. Louis, Mo.). Agar was purchased from BD (sparks, MD).

Lauric acid monoglyceride was purchased from TCI (Tokyo Chemical Industry), *Trichophyton rubrum* strain 216-3664 was obtained from fungal laboratory of Huashan Hospital, *Aspergillus fumigatus* 116-7490 was obtained from fungal laboratory of Huashan Hospital, PDA finished dry powder was purchased from Merck (Germany), and RPMI1640 was purchased from GIBCO (United States).

Culture of Bacterial:
MRSA252 strain (obtained from ATCC) was removed from the frozen state and grown on tryptic soy agar plates at 37° C. overnight. Then a single colony was inoculated in Tryptic Soybean Medium (TSB) and incubated at 37° C. with shaking until $OD_{600}$ of the culture reaching around 0.7 (logarithmic growth phase). Bacteria were then obtained upon centrifugation at 4000*g for 3 minutes and washed twice with sterile PBS. After removal of PBS by centrifugation, the bacteria obtained were suspended in appropriate amount of fresh TSB for later use.

*Propionibacterium acnes* (ATCC 6919) was cultured in Brinell medium supplemented with 5% (v/v) defibrinated sheep blood, vitamin K (5 μg/mL) and Hematin chloride (50 μg/mL), and cultured in an anaerobic environment at 37° C. generated by the aspirator. Monoclones colonies were picked and inoculated into intensive *Clostridium* medium medium and cultured anaerobically at 37° C. until $OD_{600}$ reaching approximately 1.0 (logarithmic growth phase). After centrifugation at 5000 g for 10 minutes, the cells were collected and washed with PBS, and then reconstituted with an appropriate amount of PBS for testing.

*Helicobacter pylori* Sydney strain 1 (HPSS1 from ATCC) was removed from the frozen state and stored at 37° C. under a microaerobic conditions (10% $CO_2$, 85% $N_2$ and 5% $O_2$) in Columbia agar (containing 5% lysed horse blood (FBS)). In the experiment, fresh colonies grown on agar plates were inoculated into brain heart infusion (BHI) supplemented with 5% fetal bovine serum and then gently shaken back and forth overnight under a microaerobic conditions at 37° C. and cultured overnight so as to obtain *Helicobacter pylori* broth culture. Overnight broth cultures of HPSS1 were centrifuged at 5000*g for 10 minutes to obtain bacterial pellets. After removing the medium by centrifugation, the obtained bacteria were suspended in an appropriate amount of fresh BHI containing 5% FBS for use.

Culture of Fungi:
*Trichophyton rubrum* strains 216-3664 and *Aspergillus fumigatus* 116-7490 were removed from the frozen state and inoculated on PDA plates and cultured for 48 h at 37° C.

Preparation and Characterization of Nanoparticles of the Invention: A mixture of 200 mg of surfactant (polysorbate 20 or polysorbate 80) and lipid (egg yolk lecithin:cholesterol=9:1 weight ratio) was suspended in 4 mL of water, wherein the ratio of surfactant:liposomes is 10:0, 8:2, 5:5, 3:7, 1:9, or 0:10, respectively. The suspension was stirred until a homogeneous solution is formed which was then heated above the melting point of the surfactant and lipid (20° C., 30° C., 40° C., 50° C., 60° C., 70° C. or 80° C. depending on the used surfactant and lipid and the ratio thereof). Corresponding concentrations of fatty acids such as linolenic acid (0.1% w/v to 4% w/v), (0.1% w/v to 5% w/v), myristoleic acid or lauric acid monoglyceride (0.1% w/v to 0.8% w/v) was added to the suspension and stirred for 30 minutes. This solution was kept overnight at room temperature. The hydrodynamic size of the nanoparticles of the present invention was measured using Malvern Zetasizer ZS instrument (Malvern Instruments, England, UK). The average diameter of the nanoparticles of the present invention was determined by dynamic light scattering (DLS). All measurements of property were repeated for 3 times at 25° C.

Stability of nanoparticles of the invention: The long-term stability of the nanoparticles of the present invention was examined by storing the nanoparticle solutions at different temperatures for a certain period of time; the particle size of a sample was measured at each predetermined time point to determine the stability of nanoparticles of the invention at different temperatures.

In Vitro Antibacterial Activity (MIC and MBC Values) of the nanoparticles of the invention: In vitro MIC and MBC of the nanoparticles of the invention for different bacteria were tested using conventional methods in the art.

Morphology of the bacteria treated with the nanoparticles of the present invention: The morphology of the bacteria treated or not treated with the nanoparticles of the present invention was measured by a conventional method using a scanning electron microscope (SEM).

Determination of In vivo antibacterial activity of nanoparticles of the present invention against MRSA252:

In vivo antibacterial activity and therapeutic effects of the nanoparticles of the invention on MRSA252 infection were evaluated in following two models: mouse epidermal wound infection model and mouse subcutaneous infection model.

To establish an epidermal wound model, mice (from Charles River laboratories) were intraperitoneally injected with ketamine and xylazine. After anesthesia, black hairs of the mice were shaved and the skin was washed with a pad of ethanol. Dermal abrasion wounds were made on the back of the epidermis of a mouse and 6*6 cross lines were made with 28 G needles in the designated 1*1 $cm^2$ area. The scratches were made in such a way that they only scratched the stratum corneum and epidermis while not the dermis. After 5 minutes, 50 μL of suspension in PBS containing $1 \times 10^7$ CFU of MRSA252 was seeded using a micropipette into the cross scratched area. After 30 minutes, PBS gel of the nanoparticles of the invention was used in the lesion area. The used gel was a hydrogel prepared from hydroxyethyl cellulose, glycerol, polyethylene glycol at a proper ratio. These drugs were applied daily for 5 consecutive days. Blank suspension gel was also applied as a control experiment. Mice were euthanized on day 6; skin tissue was removed by 8 mm skin punch and the number of included bacteria was counted.

To establish a subcutaneous infection model, black hairs of mice were shaved and the skin was washed with a pad of ethanol. Afterwards, 20 μL of suspension in PBS containing $1 \times 10^6$ CFU of MRSA 252 was subcutaneously injected into the shaved area, followed by injection of 200 μL of the nanoparticles of the present invention in the same area. Sterile PBS was injected as a blank control experiment. Physiological appearances and patterns at the site of infection were carefully observed. Three days after bacterial inoculation, results of histological analysis on the wounds were recorded.

Determination of in vivo antibacterial activity of the nanoparticles of the present invention against *P. acnes*: the antibacterial activity of the nanoparticles of the invention against *P. acnes* under physiological conditions was examined through intradermal injection of ICR mice (from Charles River laboratories). In particular, *P. acnes* ($1 \times 10^7$ CFU, dissolved in 20 μL of PBS) was intradermally injected into both ears of ICR mice (including the left and right ears), and then nanoparticles of the present invention (1% w/v lauric acid) or PBS (used as a negative control test) were injected at the injection site of *P. acnes*, respectively. 24 hours after injection, mouse ear samples were harvested by 8 mm biopsy perforation and then homogenized in 1 mL of sterile PBS (Mini-Beadbeater™). Homogenates were diluted with PBS at a dilution ratio of 1:10 to $1:10^6$. 10 μL of each dilution was taken and plated onto RCM agar plates. The agar plates were incubated at 37° C. for 3 days in the absence of oxygen and then the CFU of *P. acnes* was counted again. Six mice per group (n=6) were used and the experiment was repeated for three times to verify the statistical significance.

Study on in vivo toxicity of the nanoparticles of the invention (1% w/v linolenic acid): skin toxicity of the nanoparticles of the present invention was tested using the back skin of ICR mice. In particular, the back of the mouse was shaved 24 hours before study. Then, the shaved area was applied with the nanoparticle gel of the invention once daily in 7 days. Mice that were smeared with PBS were used as a control group. In order to avoid drying the gel, the skin of the mouse was covered with gauze. 24 hours after the last topical administration, the mice were euthanized and the skin was sectioned 8 mm cross-section for histological examination. Skin tissue of each mouse was treated in 10% buffered formalin for 18 hours and then embedded into paraffin. These tissue sections were stained by H & E method. Apoptosis of epithelial cell was evaluated by TUNEL assay. Sections were then imaged with Hamamatsu NanoZoomer2.0HT (Digital Slice Scanner). Images were processed using NDP image software. Five mice per group (n=5). To assess toxicity, tissue samples were scored on Draize scale. Scoring system is as follows: 0—no evidence of irritation; 1—extremely small, almost imperceptible; 2—clear and visible stimulation in epidermis; 3—severe irritation in epidermis; 4—severe irritation in epidermis with dermal stimulation; 5—severe irritation in epidermal and dermal layers. To analyze macrophage infiltration, 8 mm section sections of skin tissue of a mouse were harvested. These frozen skins were sectioned, skin macrophages were stained with FITC-anti-mouse f4/80 antibody and nuclei were stained with DAPI. After staining, skin samples were immediately imaged with Nikon Delta Macroview fluorescence microscope.

Skin Toxicity: skin toxicity of the nanoparticles of the present invention was tested on the back skin of ICR mice. In particular, 24 hours before the study, mice were shaved on their backs and then topically administered with a cellulose gel of the nanoparticles of the present invention (1% w/v lauric acid) (a hydrogel prepared from hydroxyethylcellulose, glycerol, polyethylene glycol in an appropriate ratio). Blank PBS gel (without the nanoparticle of the invention) was used as a negative control. 24 hours later, the morphology of the skin was examined and photographed. The skin irritation results were scored according to Draize scoring system. Sections of the skin were taken through 8 mm biopsy perforation, stained with hematoxylin and eosin (H & E) and photographed with a microscope to observe the histology of the skin. Six mice per group (n=6) were used and the experiment was repeated for three times to verify the statistical significance.

Determination of in vitro anti-fungal activity (MIC) of the non-vesicular nanoparticles of the present invention: Colonies of *Trichophyton rubrum* strain 216-3664 cultured on PDA plates were picked and placed into sterile double-distilled water and formulated into a liquid with a turbidity of $10^6$ CFU, and then diluted for 1000 times with RPMI 1640 liquid to a final bacterial concentration of $10^3$ CFU. A 96-well plate with lid was taken, the double-diluted drug solution was added to the 96-well plate from high to low concentration respectively, wherein 100 μl of drug solution was added into each well 1-10, 100 μl of RPMI 1640 liquid medium (containing no drug solution) was added into well 11 as positive control, 200 μl of RPMI 1640 liquid medium (containing no drug solution) was added to well 12 as negative control. 100 μl of bacterial suspension was added into well 1-11 respectively. A row of holes were prepared for each strain, and parallel operation was performed for 1 time. The prepared culture plate was placed in a humidified incubator at 35° C. for 48 h, and MIC value of the drug was obtained by observing the lowest concentration of the drug solution at which the strain did not grow.

A similar procedure was used to measure in vitro MIC values of non-vesicular nanoparticulates of the invention against *Aspergillus fumigatus* 116-7490. In particular, colonies of *Aspergillus fumigatus* 116-7490 cultured on a PDA plate was picked and placed into sterile double-distilled water and formulated into a liquid with a turbidity of $10^6$ CFU. MIC determination method was the same as the method for determining *Trichophyton rubrum* strain 216-3664.

Example 1. Preparation and Characterization of Nanoparticles of the Invention

The nanoparticles of the present invention were prepared as described in the "Materials and Methods" section.

The hydrodynamic particle size of the nanoparticles of the present invention is described by two parameters: z-average particle size and polydispersity index, both of which are calculated by cumulant analysis of dynamic light scattering measurements.

By varying concentration of linolenic acid, a series of nanoparticles were prepared by the inventors and tested to determine the optimal dosage form. As shown in FIG. 1A, the solution appears clear and transparent (d) when the concentration of linolenic acid is 1% w/v, wherein the average particle diameter of the nanoparticles of the present invention is 10 nm, and polydispersity index is 0.2. Therefore, the nanoparticles selected in subsequent experiments contained 1% w/v linolenic acid with a mass ratio of lipid to surfactant as 2:1 (also referred to herein as TNAN-2). In addition, the present inventors also examined that the surface potential of the nanoparticles of the present invention in water is between −3 mV and −6 mV when the concentration of contained linolenic acid was between 0.2% w/v and 0.9% w/v.

By varying the concentration of lauric acid, a series of nanoparticles of the present invention were prepared by the present inventors and the best formulation was identified through repeated experiments. As shown in FIG. 1B, the solution appeared clear and transparent (c) when the concentration of lauric acid was 1% w/v, and the average diameter of the nanoparticles was 11.1 nm and the average polydispersity index was 0.09. Therefore, the formulation selected in subsequent experiments was 1% w/v lauric acid (mass ratio of lipid to surfactant as 2:1, also referred to herein as TNAN-1). In addition, the present inventors also examined that the surface potential of the nanoparticles of the present invention in water was −5 mV to −15 mV.

Figure 2:
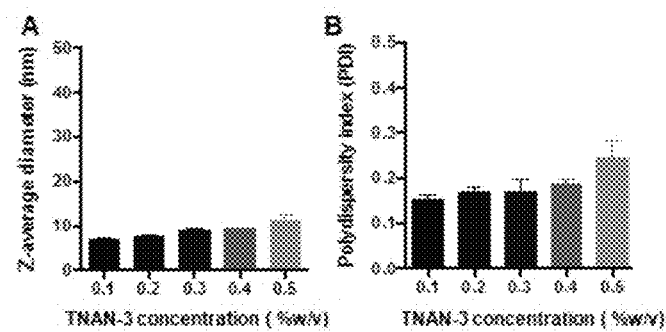
FIG. 2 shows (A) hydrodynamic size (diameter, nm) and (B) polydispersity (PDI) of nanoparticles of the present invention containing different concentrations of myristoleic acid detected by dynamic light scattering.

The present inventors also prepared nanoparticles of the present invention at different loading rates of myristoleic acid of 0.1-4% w/v, as shown in FIG. 1C, to select the optimal yield of nanoparticles while maintaining acceptable nanoparticle size (about 9 nm). The present inventors found that as the initial loading concentration of myristoleic acid increases, the nanoparticle size also increases (FIG. 2). The best formulation selected for subsequent experiments was 0.3% w/v myristoleic acid (mass ratio of lipid to surfactant as 2:1, also referred to herein as TNAN-3) with an average particle size of about 8.6 nm and threshold below 10 nm. The mass of the nanoparticles was measured by dynamic light scattering and characterized by the polydispersity parameter. PDI of nanoparticles containing 0.3% w/v myristoleic acid was about 0.2, indicating a relatively narrow particle size distribution.

The inventors also determined the incorporation of myristoleic acid into the nanoparticle formulations of the present invention by surface Z-potential. The surface Z-potential of formulations loaded with 0.1-0.5% w/v myristoleic acid in deionized water ranged from −3 to −13 mV. The higher loading of myristoleic acid in the formulation resulted in more negative surface charges. Such decrease in surface z-potential correlates with loading of myristoleic acid due to incorporation of myristoleic acid into the nanoparticles of the present invention, since the carboxylic acid groups of myristoleic acid will be deprotonated near physiological pH 7.4 to become $COO^-$.

Figure 34:
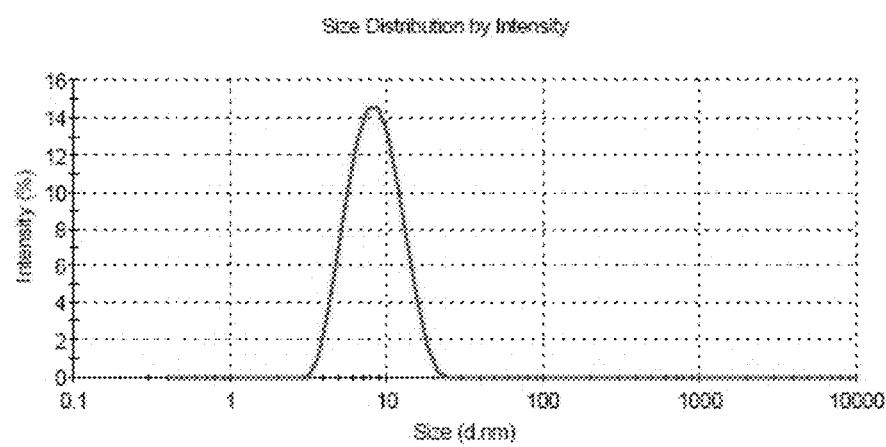
FIG. 34 shows the size distribution curve of the nanoparticles of the invention (0.4% w/v lauric acid monoglyceride).

A series of non-vesicular nanoparticles containing different concentrations of lauric acid monoglyceride (0.1-0.8% w/v) were also prepared by the present inventors and tested to determine the optimal dosage form. When the concentration of lauric acid monoglyceride was 0.4 wt %, the solution appeared clear and transparent (as shown in FIG. 1D), wherein the average particle diameter of the nanoparticles was 7.5 nm and the average polydispersity index was 0.17 (as shown in FIG. 34).

Example 2-1. In Vitro Antibacterial Activity of the Nanoparticles of the Invention-1

Figure 8:
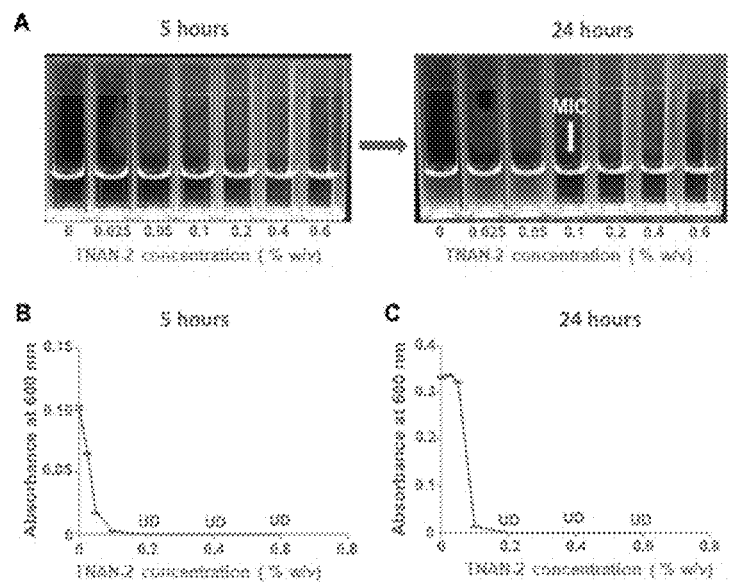
FIG. 8 shows in vitro minimum inhibitory concentration (MIC) of nanoparticles of the inventive containing 1% w/v linolenic acid on MRSA252. Different concentrations of nanoparticles were incubated with MRSA252 ($1*10^6$ CFU/mL) (CFU: colony forming unit) and the absorbance of the bacteria at $OD_{600}$ was measured at 5 hours and 24 hours, respectively. The results show that the nanoparticles of the present invention are capable of inhibiting the growth of bacteria at a concentration of higher than 0.1% w/v or even higher. The pictures of the mixed suspension of bacteria and the nanoparticles of the invention at 5 and 24 hours show that the solution of 0.1% w/v nanoparticle is clear and transparent, indicating that 0.1% w/v is MIC of the nanoparticles of the invention.

In vitro antibacterial activity of the nanoparticles (linolenic acid) of the present invention against MRSA252 was evaluated by examining the bacteriostatic and bactericidal effects of different concentrations of the nanoparticles of the invention when co-incubated with bacteria. In the study, the minimum concentration of nanoparticles of the present invention inhibiting bacterial growth (MIC) was firstly measured. In particular, $1 \times 10^6$ CFU of MRSA252 was co-cultured with the nanoparticles of the invention at a concentration of 0-0.6% w/v. The liquid of bacteria co-cultured with the nanoparticles of the present invention in a concentration of not less than 0.1% w/v maintained clear, indicating that at this concentration, bacterial growth was significantly inhibited (FIG. 8A). In contrast, when the concentration of the nanoparticles of the present invention was less than 0.1% w/v, the bacterial culture liquid becomes turbid, exhibiting a large amount of bacterial growth. To quantify bacterial growth, after incubating for 5 or 24 hours, $OD_{600}$ of the mixture liquid was measured to determine the number of bacteria (1 $OD_{600}$ corresponding to $10^8$ CFU/mL). As shown in FIGS. 8B and 8C, when the concentration of the nanoparticles of the present invention was higher than 0.1% w/v, the growth of bacteria was suppressed. Summing up, 0.1% w/v is MIC of the nanoparticles of the present invention against MRSA252.

Figure 11:
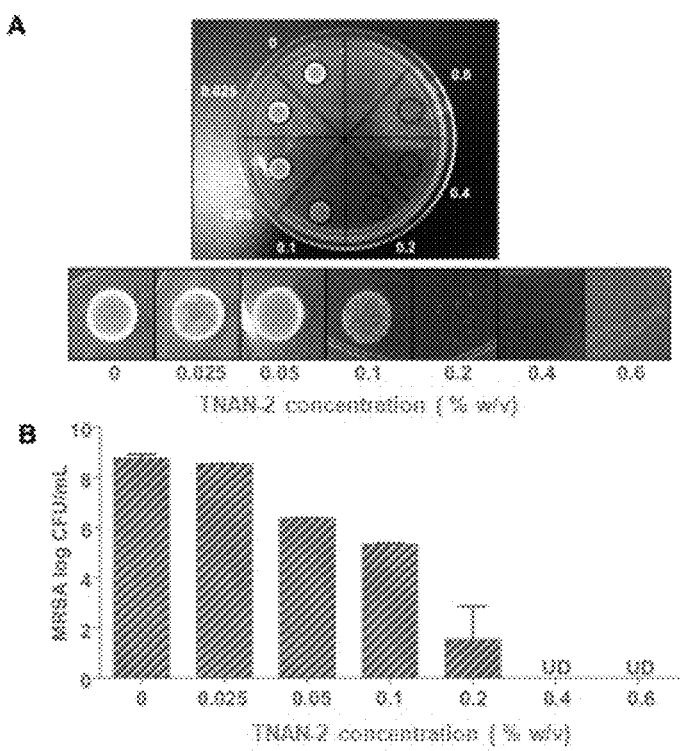
FIG. 11 shows in vitro minimum bactericidal concentration (MBC) of the nanoparticles of the invention containing 1% w/v linolenic acid against MRSA252. Nanoparticles of the invention at different concentrations were incubated with MRSA252 ($1*10^6$ CFU/mL) for 24 hours, and then 5 μL of the suspension was incubated overnight at 37° C. and observed on TSB agar plates. The CFU value of MRSA252 was quantified. (A) Images show observed CFU of MRSA252 after the nanoparticles of the invention at different concentrations were incubated with MRSA252 on agar plates for 24 hours; (B) The results show that 0.2% w/v of the nanoparticles of the invention killed 99.9% of MRSA252. Moreover, bacteria were killed altogether when the concentration of nanoparticles of the present invention reached 0.4% w/v or higher.

Minimum bactericidal concentration (MBC) of the nanoparticles of the inventive against MRSA252 was also tested. In particular, the defined MBC value was defined as the lowest antibacterial concentration capable of killing 99.9% of the target bacteria MRSA252. In one in vitro experiment, different concentrations of the nanoparticles of the invention were co-incubated with MRSA252 ($1*10^6$ CFU) for 24 hours. By such incubation, the nanoparticles of the invention were allowed to contact with MRSA252 and kill bacteria. After incubation, 5 µL of the bacterial culture was taken and placed on an agar plate, followed by overnight incubation at 37° C., and then the CFU of MRSA252 was counted. FIG. 11A shows representative photographs of 5 µL sample cultured on an agar plate after different concentrations of the nanoparticles of the present invention incubated with the bacterial liquid for 24 hours. Obviously, the higher the used drug concentration, the fewer visible colonies on the agar plate. Afterwards, 5 µL of bacterial culture in each group was taken, diluted at 1:10 to $1:10^5$, and then placed on a TSB agar plate to observe and count CFU. As shown in FIG. 11B, 0.2% w/v of the nanoparticles of the invention killed 99.9% of MRSA252. When the concentration of linolenic acid was increased to above 0.2% w/v, all the bacteria died. Therefore, 0.2% w/v is the MBC value of the nanoparticles of the present invention against MRSA252.

The above results show that the ratio of MBC:MIC of the nanoparticles of the present invention against MRSA252 was approximately 2:1, indicating that the nanoparticle is a bactericide for this bacterium. At the same time, this nanoparticle reduced the number of bacteria by 3 logs in 24 hours, demonstrating the bactericidal effect of this nanoparticle on MRSA. This study can guide the future evaluation of the concentration and duration of drug exposure in vivo.

Figure 17:
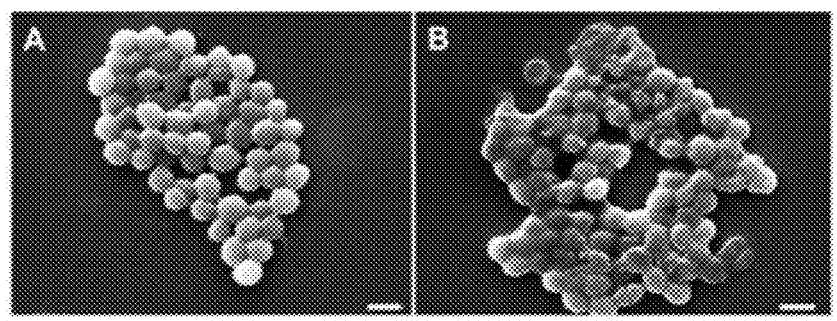
FIG. 17 shows morphology of MRSA252 before (A) and after (B) treated with nanoparticles of the invention containing 1% w/v linolenic acid. In (B), bacteria were imaged after incubated with the nanoparticles of the invention for 24 hours. In all experiments, the initial bacterial concentration was $1*10^6$ CFU/mL. The scale in the picture is 1 μm.

For deeply understanding the mechanism by which the nanoparticles of the present invention kill MRSA252, the present inventors further examined the morphological changes of MRSA252 bacteria before and after treated by the nanoparticles of the present invention. Before treatment, MRSA252 cells were in a grape-like form with a typical diameter of 0.6-1 µm according to SEM images, aggregated morphology and intact cell wall/membrane structure (FIG. 17A). After treated with the nanoparticles of the present invention for 24 hours, SEM imaging showed substantial changes in bacterial morphology, including significant disruption of cell structure, irregular aggregate morphology, and blurry cell edges (FIG. 17B). Such changes in morphology mean that the nanoparticles of the present invention have strongly devastating effects on bacterial cells, thereby inhibiting bacterial growth.

Example 2-2. In Vitro Antibacterial Activity of the Nanoparticles of the Invention-2

Figure 12:
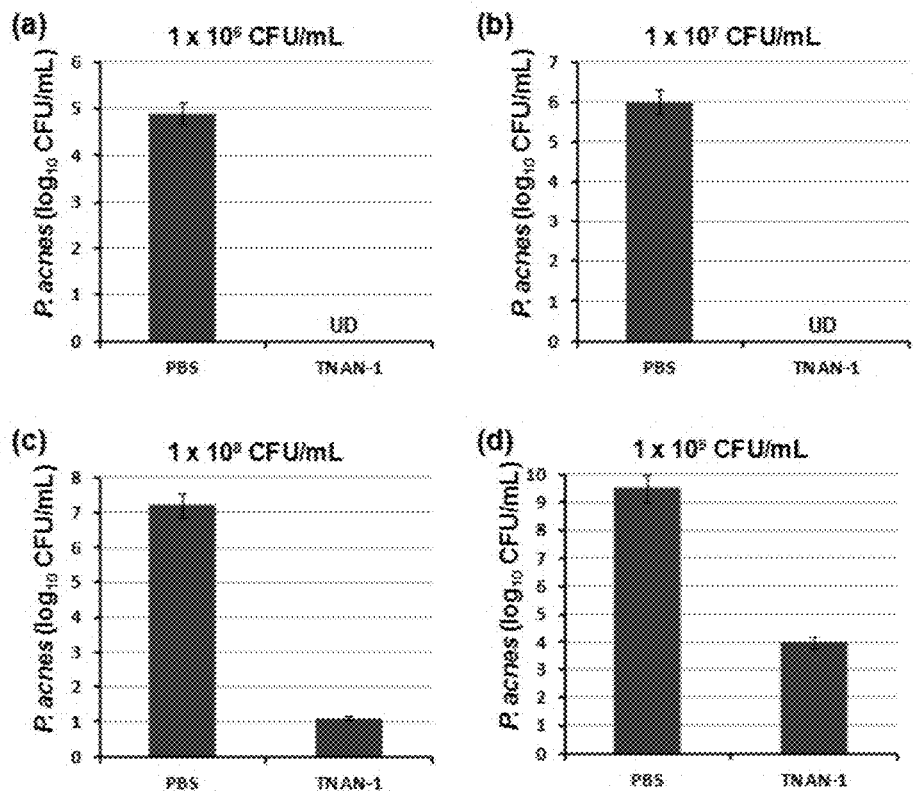
FIG. 12 is a graph showing the antibacterial activity of nanoparticles of the present invention (1% w/v lauric acid) against different concentrations of P. acnes: (a) $1\times10^6$ CFU/mL, (b) $1\times10^7$ CFU/mL, (c) $1\times10^8$ CFU/mL and (d) $1\times10^9$ CFU/mL. Nanoparticles of the invention were incubated with each concentration of bacterial sample for 5 hours. Afterwards, the samples were diluted with PBS at a dilution of 1:10 to $1:10^6$ and 10 μL of each sample was seeded onto RCM agar plates. CFUs of P. acnes were counted (UD: undetectable) after cultured at 37° C. for 3 days under anaerobic conditions.

The nanoparticles of the present invention (1% w/v lauric acid) was co-incubated with different concentrations of $P.$ $acnes$ ($1 \times 10^6$ CFU/mL, $1 \times 10^7$ CFU/mL, $1 \times 10^8$ CFU/mL and $1 \times 10^9$ CFU/mL) at 37° C. for 5 hours to test in vitro antibacterial activity thereof. After co-incubation, samples were diluted with PBS at a dilution of 1:10 to $1:10^6$ and then 10 µL of each sample was taken and plated on RCM agar plates. Samples were incubated for 3 days at 37° C. in anaerobic conditions and then CFUs of $P.$ $acnes$ were counted. As shown in FIG. 12, the nanoparticles of the invention can completely kill $P.$ $acnes$ when the bacterial concentration was below $1 \times 10^7$ CFU/mL. When the bacterial concentration increased to $1 \times 10^9$ CFU/mL, the nanoparticles of the present invention can reduce bacterial load by up to 5 orders of magnitude with a residual bacterial concentration of approximately $1 \times 10^4$ CFU/mL, which means that at high concentrations of bacteria, the nanoparticles (1% w/v lauric acid) are not sufficient to eliminate all bacteria, probably due to the insufficient amount of nanoparticles in solution.

Figure 13:
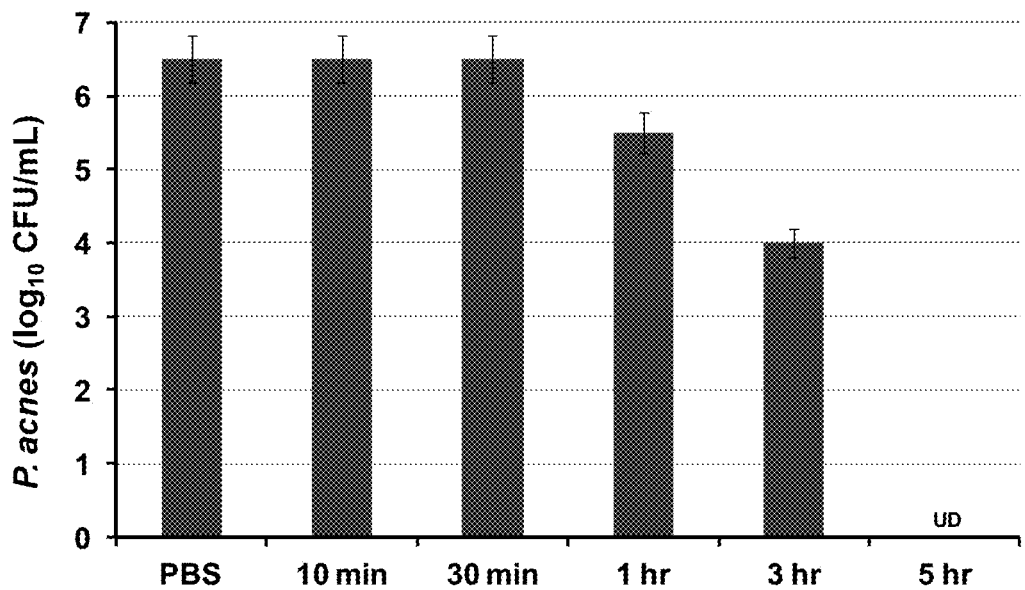
FIG. 13 shows a graph of the antibacterial activity vs time of nanoparticles of the present invention (1% w/v lauric acid) against $1\times10^7$ CFU/mL of P. acnes. P. acnes were completely killed after incubated for 5 hours (UD: undetectable).

The results of the time-dependent antibacterial activity test of the nanoparticles of the present invention show that the bacterium can be completely killed only when the nanoparticles of the present invention are co-incubated with bacteria ($1 \times 10^7$ CFU/mL) for 5 hours. As co-incubation time decreased, antibacterial properties also decreased (FIG. 13).

Figure 14:
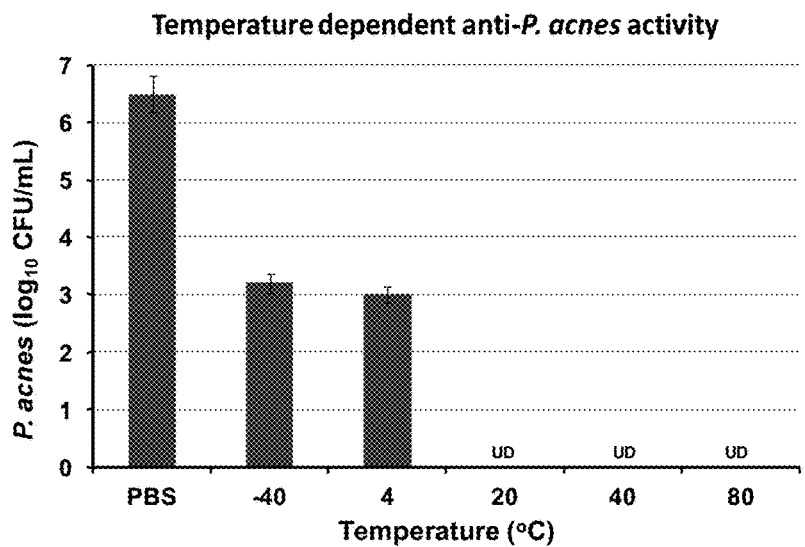
FIG. 14 shows a graph of the antibacterial activity vs temperature of nanoparticles of the present invention (1% w/v lauric acid) against $1\times10^7$ CFU/mL of P. acnes after incubated for 5 hours. The results showed that P. acnes were completely killed (UD: undetectable) at room temperature (20° C.) or higher.

Such antibacterial activity of the nanoparticles of the present invention is also related to the operating temperature. After the nanoparticles (1% w/v lauric acid) were co-incubated with bacteria ($1 \times 10^7$ CFU/mL) for 5 hours, the results showed that the bacteria were completely eliminated at room temperature (20° C.) or higher (FIG. 14).

Figure 9:
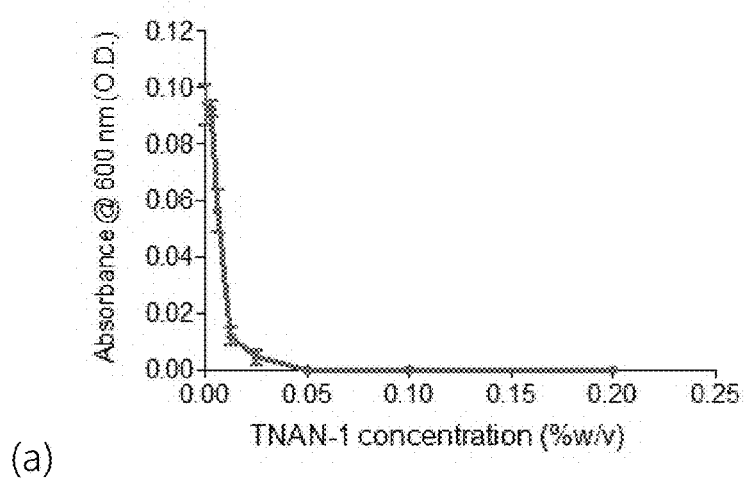
FIG. 9 shows in vitro minimum inhibitory concentration (MIC) of the nanoparticles of the invention containing 0.1% w/v lauric acid against P. acnes, wherein Figure (b) is an enlargement of Figure (a).
Figure 9:
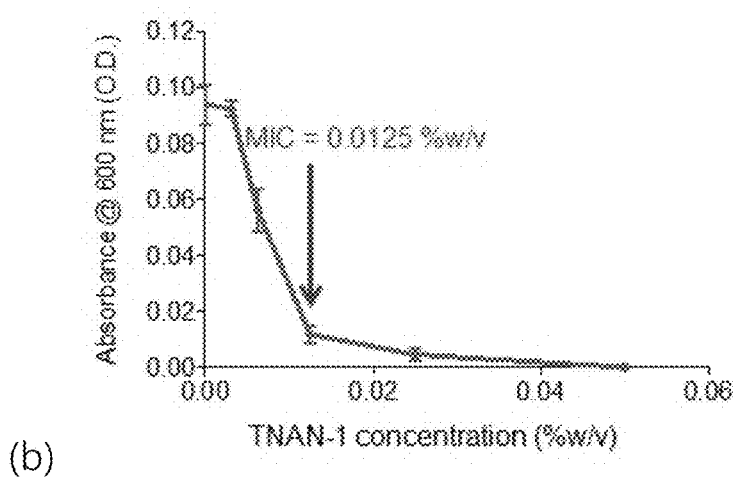

To determine in vitro MIC of the nanoparticles of the invention against $P.$ $acnes$, different concentrations of the nanoparticles of the invention were incubated with $P.$ $acnes$ ($1*10^6$ CFU/mL) for 5 hours under anaerobic conditions and absorbance at 600 nm were tested for the samples (optical density at 600 nm, $OD_{600}$). All tests are run in parallel for three times. The results show that when the concentration of the nanoparticles of the present invention is 0.0125% w/v or higher, they inhibit the growth of bacteria as shown in FIG. 9.

Figure 15:
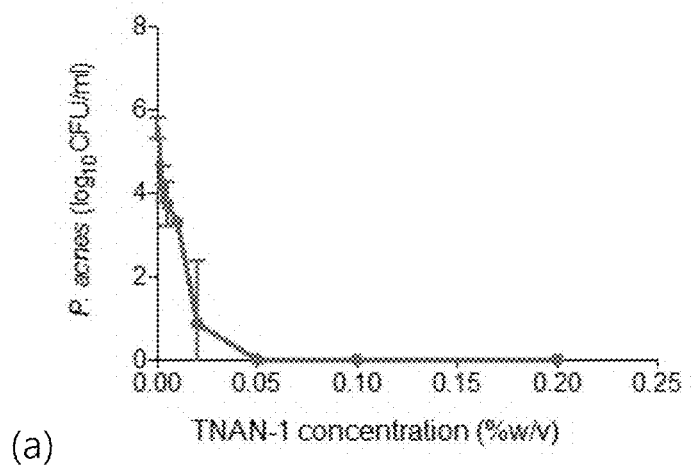
FIG. 15 shows in vitro minimum bactericidal concentration (MBC) of nanoparticles of the present invention containing 1% w/v lauric acid against P. acnes, wherein Figure (b) is an enlargement of Figure (a).
Figure 15:
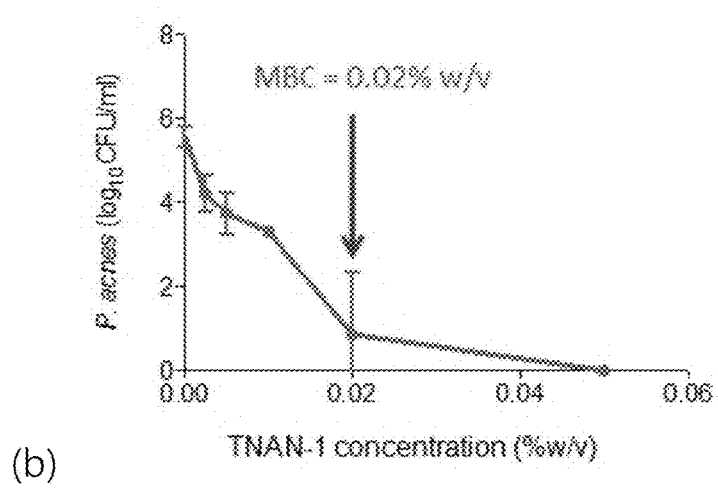

To determine in vitro MBC of the nanoparticles of the invention against $P.$ $acnes$, different concentrations of the nanoparticles of the invention were incubated with $P.$ $acnes$ ($1*10^6$ CFU/mL) for 5 hours under anaerobic conditions at 37° C. After incubation, the samples were diluted at 1:10 to $1:10^6$ with PBS and 5 µL of the dilution was seeded on a RCM agar plate. The agar plate was cultured under anaerobic conditions at 37° C. for 3 days, after which CFU (colony forming unit) of $P.$ $acnes$ was quantitatively determined. The results show that 0.02% w/v of the nanoparticles of the invention killed 99.9% of $P.$ $acnes$. In addition, the nanoparticles of the invention at 0.05% w/v and higher killed all of the bacteria, as shown in FIG. 15.

The above results show that the ratio of MBC:MIC of the nanoparticles of the present invention to $P.$ $acnes$ was approximately 1.6:1, indicating that the nanoparticle is a bactericide for this bacterium.

Figure 18:
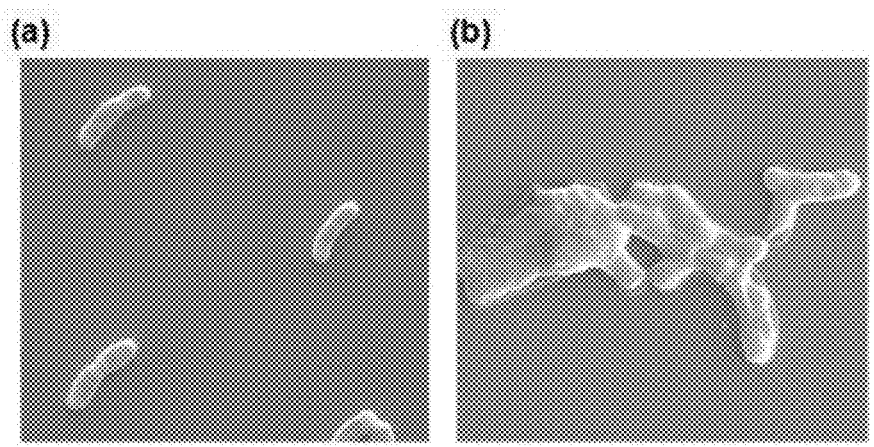
FIG. 18 shows scanning electron microscopy (SEM) pictures of: (a) untreated P. acnes, (b) P. acnes treated with nanoparticles of the invention containing 1% w/v lauric acid. It is showed by electron microscopy that the bacterial membrane of P. acnes was destroyed after treated with the nanoparticles of the present invention.

After quantitative analysis of in vitro antibacterial activity of the nanoparticles of the present invention against $P.$ $acnes$, the effects of the treatment using the nanoparticles on the morphology of the bacteria was observed with a scanning electron microscope. $Propionibacterium$ $acnes$ were co-incubated with the nanoparticles for 5 hours, fixed with 2% glutaraldehyde and then observed with a scanning electron microscope. As shown in FIG. 18, a scanning electron micrograph of an untreated sample (i.e., co-incubated with PBS buffer) shows that $P.$ $acnes$ has a regular rod-like structure with smooth surface and pili. In contrast, the bacteria treated with the nanoparticles of the present invention showed significant abnormalities; irregular deformations and constrictions are present on the bacterial surface, no pili (FIG. 18). The above results show that the nanoparticles of the present invention may destroy the structure of the bacterial membrane to exert its bactericidal function.

Example 2-3. In Vitro Antibacterial Activity of the Nanoparticles of the Invention-3

In vitro antibacterial activity of the nanoparticles of the present invention (myristoleic acid) against $H.$ $pylori$ (Sydney Strain 1, HPSS1) was determined by MIC (defined as the lowest concentration that inhibits bacterial growth) and MBC (defined as the lowest concentration that kills 99.9% of target bacteria) value against $H.$ $pylori$.

Figure 10:
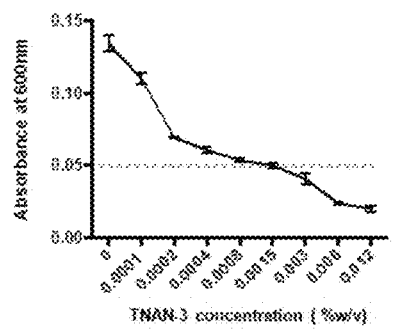
FIG. 10 shows in vitro minimum inhibitory concentrations (MIC) of the nanoparticles of the invention containing 0.3% w/v myristoleic acid against H. pylori (Sydney Strain 1, HPSS1). Different concentrations of the nanoparticles of the invention were incubated for 18 hours with HPSS1 ($5*10^6$ CFU/mL) (CFU: colony forming unit) and the absorbance of the bacteria at $OD_{600}$ was measured. The results show that the nanoparticles of the present invention can effectively inhibit the growth of bacteria at a concentration of greater than or equal to 0.0015% w/v, indicating that 0.0015% w/v is MIC for the nanoparticles of the present invention.

To determine MIC, $H.$ $pylori$ at 0.05 $OD_{600}$ (corresponding to $5 \times 10^6$ CFU/mL) was co-cultured with the nanoparticles of the invention at different concentrations (0 to 0.012% w/v). To quantify bacterial growth, $OD_{600}$ values of bacterial cultures were determined after 18 hours of culture, and the change in value compared with the initial value was recorded. The change reflects the growth of the bacteria under the influence of the nanoparticles of the present invention. As shown in FIG. 10, when the concentration of the nanoparticles of the present invention was less than 0.0015% w/v, $OD_{600}$ value after co-cultivation varied significantly (>5%) from the initial value, suggesting that even In the presence of TNAN-3 at this concentration, the bacteria growth is obvious. On the contrary, when the concentration of myristoleic acid is higher than 0.0015% w/v, the change of $OD_{600}$ is less than 5%, indicating that bacterial growth is effectively inhibited. Therefore, 0.0015% w/v was determined as MIC of the nanoparticles of the present invention.

Figure 16:
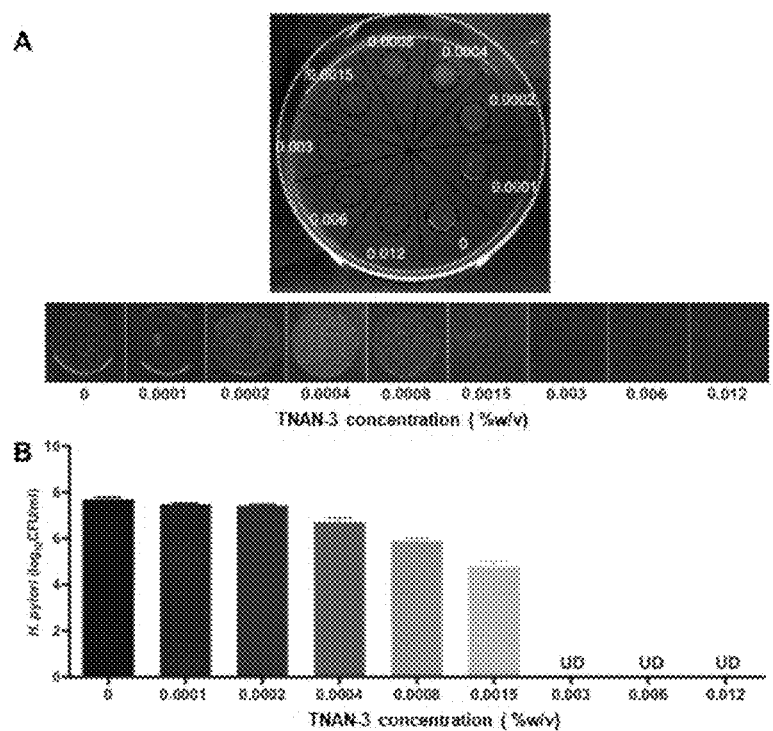
FIG. 16 shows in vitro minimum bactericidal concentrations (MBC) of nanoparticles of the present invention containing 0.3% w/v myristoleic acid against HPSS1. Different concentrations of TNAN-3 were incubated with HPSS1 ($5*10^6$ CFU/mL) for 18 hours and then 5 μL of the suspension was incubated overnight at 37° C. CFU values of HPSS1 can be quantified. (A) Images show CFU of HPSS1 observed after nanoparticles of the invention at different concentrations were incubated with HPSS1 on an agar plate for 18 hours. (B) The results show that 0.0015% w/v of nanoparticle of the invention killed 99.9% of HPSS1. Moreover, bacteria are completely killed when the concentration of nanoparticles of the present invention reached 0.003% w/v or higher.

The present inventors also determined the bactericidal effects of the nanoparticles of the present invention on *H. pylori*. *Helicobacter pylori* ($5 \times 10^6$ CFU) and different concentrations of the nanoparticles of the invention were co-cultured for 18 hours. By such culturing process, the nanoparticles of the present invention are allowed to interact with *H. pylori*, thereby killing them. After incubation, 5 μL of bacterial broth was inoculated on Columbia agar, and then incubated at 37° C. for 4 days for counting the number of bacteria. FIG. 16A shows representative photographs of 5 μL of bacteria cultured on an agar plate after treated with different concentrations of the nanoparticles of the present invention for 18 hours. Obviously, the higher the concentration of nanoparticle of the present invention, the fewer visible colonies on the agar plate.

As shown in FIG. 16B, 0.0015% w/v of the nanoparticle of the present invention killed 99.9% of *H. pylori*. When the concentration of myristoleic acid increased above 0.0015% w/v, all the bacteria died. Therefore, 0.0015% w/v is MBC value of the nanoparticles of the invention against *H. pylori*.

The results of the present invention show that the ratio of MBC:MIC of the nanoparticles of the present invention against HPSS1 is around 1:1, indicating that the formulation is a bactericide for this pathogen. While this formulation reduced bacterial counts by more than three orders of magnitude within 18 hours, indicating bactericidal effects of the drug on HPSS1, thereby providing guidance for further in vivo evaluation of the concentration and duration of drug exposure.

Figure 19:
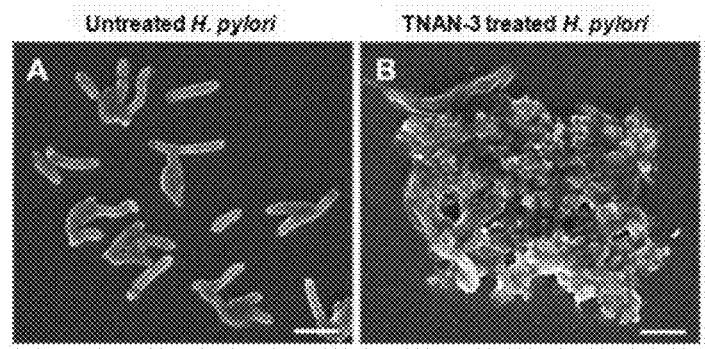
FIG. 19 shows the morphology of HPSS1 before (A) and after (B) treated with nanoparticles of the inventive containing 0.3% w/v myristoleic acid. In (B), the bacteria were imaged after incubated with 0.003% w/v of the nanoparticles of the invention for 18 hours. In all experiments, the initial bacterial concentration was $2.5*10^6$ CFU/mL. The scale in the picture is 1 μm.

For deeply understanding the mechanism by which the nanoparticle preparation of the present invention kills *Helicobacter pylori*, the present inventors further examined the morphological changes of *Helicobacter pylori* cells before and after treated by the nanoparticles of the present invention. Before treatment, *H. pylori* cells showed a normal curved morphology and complete cell membrane according to SEM images (FIG. 19A). A typical cell of helical *Helicobacter pylori* is of 2-4 μm in length and 0.5-0.8 μm in width with visible sheath flagella. After treated with the nanoparticles of the invention for 18 hours, SEM imaging showed significant changes in bacterial morphology, including complete loss of normal curved morphology, disruption of the protoplast cylinder type, lysis of cells, fragmentation of bacterial cell membranes and severe agglomeration (FIG. 19B). Such change in morphology indicates a strong destructive effect of the nanoparticle formulation of the present invention, thereby inhibiting bacterial growth.

Examples 2-4. In Vitro Antibacterial Activity of the Nanoparticles of the Invention-4

In vitro antibacterial activity of the nanoparticles of the present invention (a series of non-vesicular nanoparticles of different concentrations of lauric acid monoglyceride) against fungi was evaluated by examining the bacteriostatic effect of different concentrations of the nanoparticles of the invention when co-incubated with fungi.

The minimum concentration of the nanoparticles of the invention (MIC) inhibiting bacterial growth was firstly measured. In particular, $1 \times 10^3$ CFU of *Trichophyton rubrum* 216-3664 was co-incubated with the nanoparticles of the invention at a concentration of 0-0.4% w/v. According to the NCCLS-M27-A3 microdilution method, after incubating for 48 hours, results were obtained, wherein the growth of bacteria represents showed no inhibition, while no bacteria growth showed antibacterial effects. The minimum concentration of the nanoparticles corresponding to no bacteria growth was MIC. Through observation, MIC value of the nanoparticles of the present invention against *Trichophyton rubrum* 216-3664 was 0.006% w/v.

In addition, $1 \times 10^3$ CFU of *Aspergillus fumigatus* 116-7490 was co-incubated with the nanoparticles of the invention at a concentration of 0-0.4% w/v. The used method is the same as that for *Trichophyton rubrum* 216-3664 and the MIC of the nanoparticles of the present invention against *Aspergillus fumigatus* 116-7490 was 0.1% w/v.

Example 3. Storage Stability of the Nanoparticles of the Invention

Figure 3:
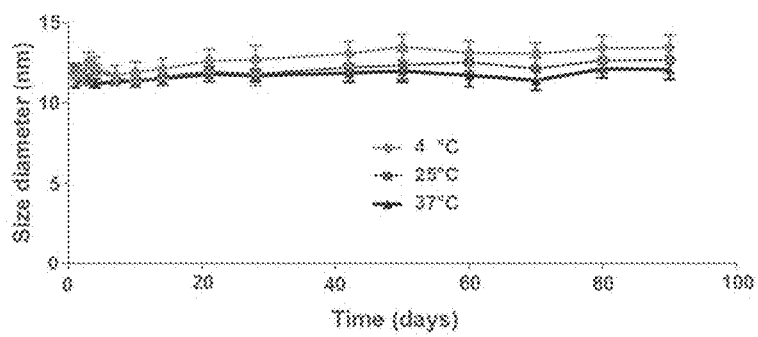
FIG. 3 shows long-term stability of the nanoparticles of the present invention containing 1% w/v linolenic acid by detecting their hydrodynamic diameter over three months. During this period, these nanoparticles were stored at 4° C., 25° C. and 37° C., respectively, with an increase in diameter of less than 2 nm.

The present inventors investigated the long-term stability of the nanoparticles of the present invention (1% w/v linolenic acid) for 3 months at different temperatures. Changes in stability were determined by measuring particle size. As shown in FIG. 3, the particle size of the nanoparticles stored at 4° C., 25° C. and 37° C. increased only from 11 nm to 13 nm with negligible variability, indicating that the nanoparticles of the present invention showed high stability under all storage conditions.

Figure 20:
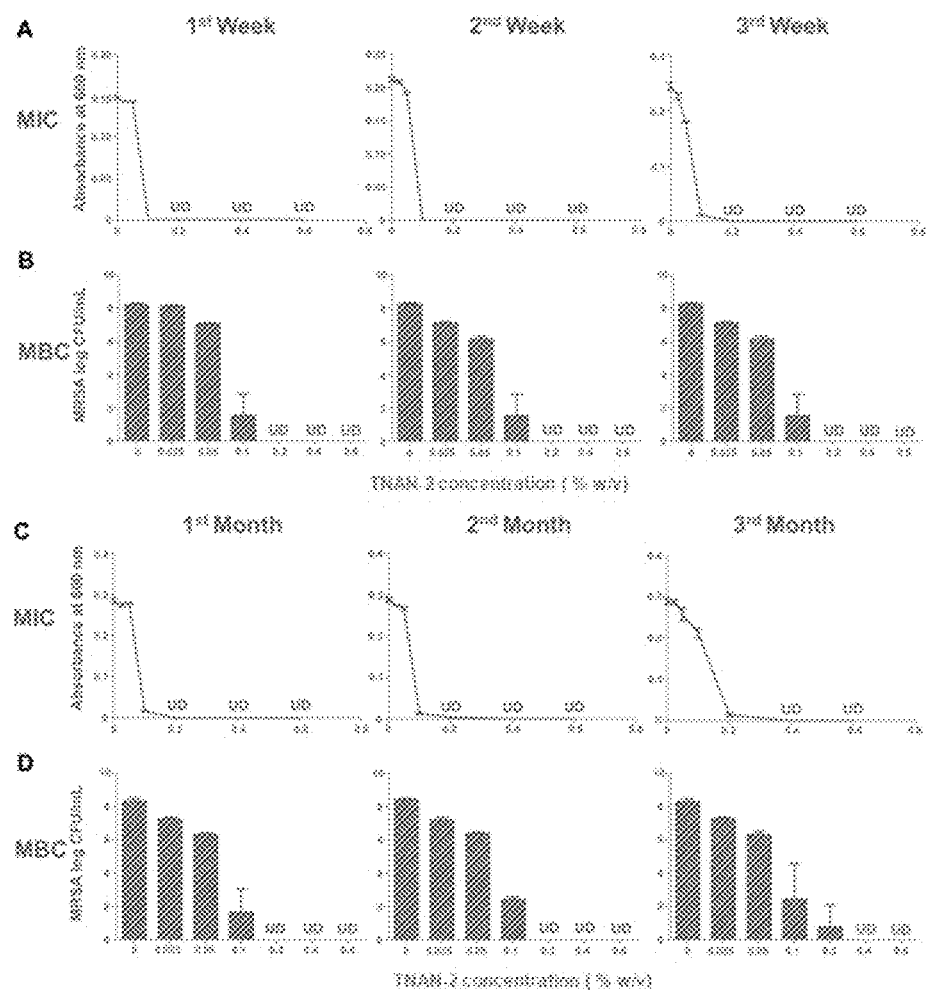
FIG. 20 shows the long-term antibacterial activity of the nanoparticles of the invention containing 1% w/v linolenic acid. After stored at room temperature for two months, the nanoparticles of the present invention showed similar MIC and MBC values with the freshly prepared nanoparticles of the present invention. After stored for 3 months, MIC of the sample slightly increased to 0.2% w/v, while the MBC value was in agreement with the previous.

As a medicament, the key point of the nanoparticles of the present invention is to maintain effective bactericidal effects over a long period of storage, that is, in addition to a stable structure, a stable activity is also very important. To assess this ability, the inventors examined MIC and MBC values of the nanoparticles of the present invention over a three-month storage period. As shown in FIG. 20, the nanoparticles of the present invention showed similar MIC and MBC values as freshly prepared samples after stored at room temperature for three months.

Figure 21:
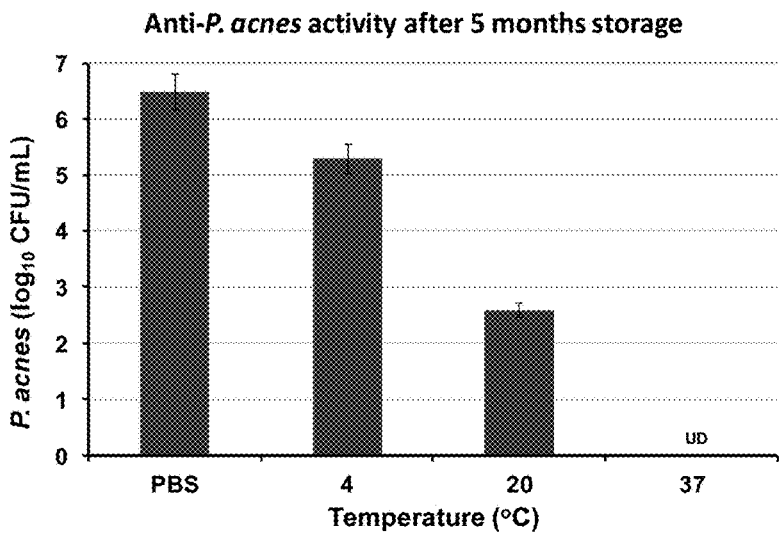
FIG. 21 shows the antibacterial activity of nanoparticles of the invention (1% w/v lauric acid) against $1\times10^7$ CFU/mL of P. acnes after stored at different temperatures for 5 months. Propionibacterium acnes were completely killed under storage condition of 37° C. (UD: undetectable).

Studies have shown that the antibacterial activity of the nanoparticles of the invention (1% w/v lauric acid) is also related to the storage temperature. After stored for 5 months at 37° C., the nanoparticles of the present invention have the same antibacterial activity as the fresh nanoparticles, which can kill $1 \times 10^7$ CFU/mL of *P. acnes* completely. However, when stored at a temperature of 20° C. or 4° C., the antibacterial activity decreased, and only an initial amount of 4.4 and 1.8 orders of magnitude of *P. acnes* ($1 \times 10^7$ CFU/mL) can be killed, respectively (FIG. 21).

Figure 4:
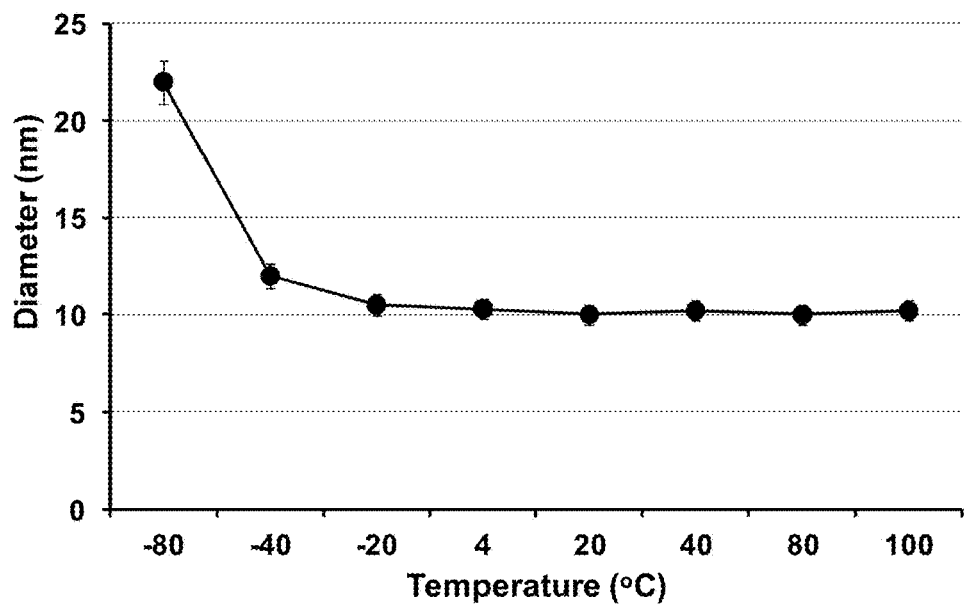
FIG. 4 shows the hydrodynamic diameter (nm) of the nanoparticles of the invention containing 1% w/v lauric acid at different temperatures over a wide range of temperatures (−40° C. to +100° C.), and the size of nanoparticles maintained stably.

Based on this, the present inventors further examined stability and efficacy of the nanoparticles of the present invention (1% w/v lauric acid) under extremely high temperature and extremely low temperature conditions. Depending on the particle size (FIG. 4) and the minimum bactericidal concentration (MBC) results (Example 2, FIG. 14), the particles are stable at 20 to 100° C. and their antibacterial activity remained unchanged. In addition, *P. acnes* at a concentration of $1 \times 10^7$ CFU/mL can not be completely eliminated by particles preserved at lower temperatures (4 to −80° C.), and TNAN-1 frozen at −80° C. was very unstable.

Figure 5:
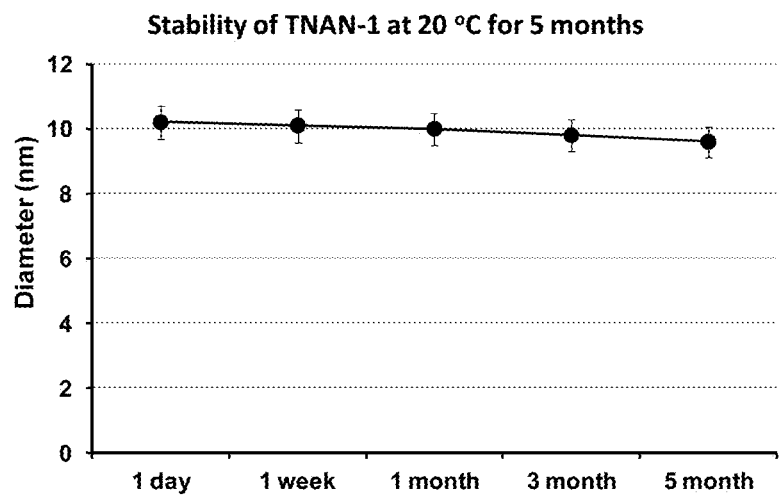
FIG. 5 shows the storage stability of the nanoparticles of the invention containing 1% w/v lauric acid at 20° C., the size of the nanoparticles maintained stably over a 5 month period of detection.

Further long-term stability tests revealed that the nanoparticles were stable for 5 months at 20° C. During the test, both of particle volume and polydispersity index remained almost constant (FIG. 5).

Figure 6:
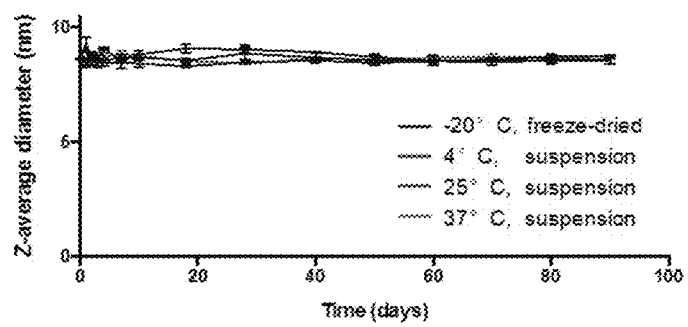
FIG. 6 shows that suspensions of nanoparticles of the invention containing 0.3% w/v myristoleic acid were stored for 3 months at −20° C., 4° C., 25° C. and 37° C., respectively, with an increase in diameter of less than 2 nm.

By monitoring the size of nanoparticle, the inventors also examined the long-term stability of other selected formulations (0.3% w/v myristoleic acid) at different storage temperatures over a three-month period of time. As shown in FIG. 6, the nanoparticle micelles preserved under various conditions including −20° C. (lyophilized formulation), 4° C., 25° C. and 37° C. (in suspension) showed a change in size between 8.2 and 9.7 nm, which can be negligible, suggesting high stability of the nanoparticles of the present invention under various storage conditions.

Figure 22:
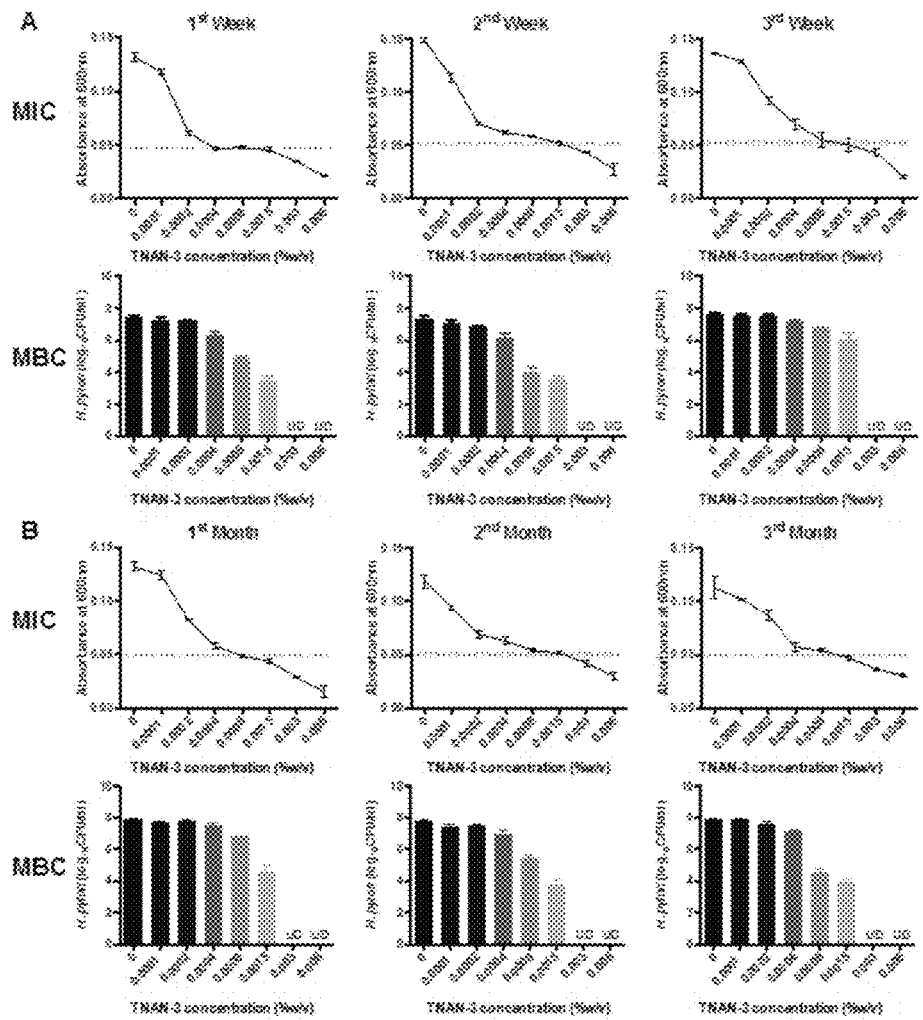
FIG. 22 shows the long-term antibacterial activity of the nanoparticles of the present invention containing 0.3% w/v myristoleic acid. After stored at room temperature for 3 months in a form of suspension, the nanoparticles showed similar MIC and MBC values as the freshly prepared nanoparticles.
Figure 23:
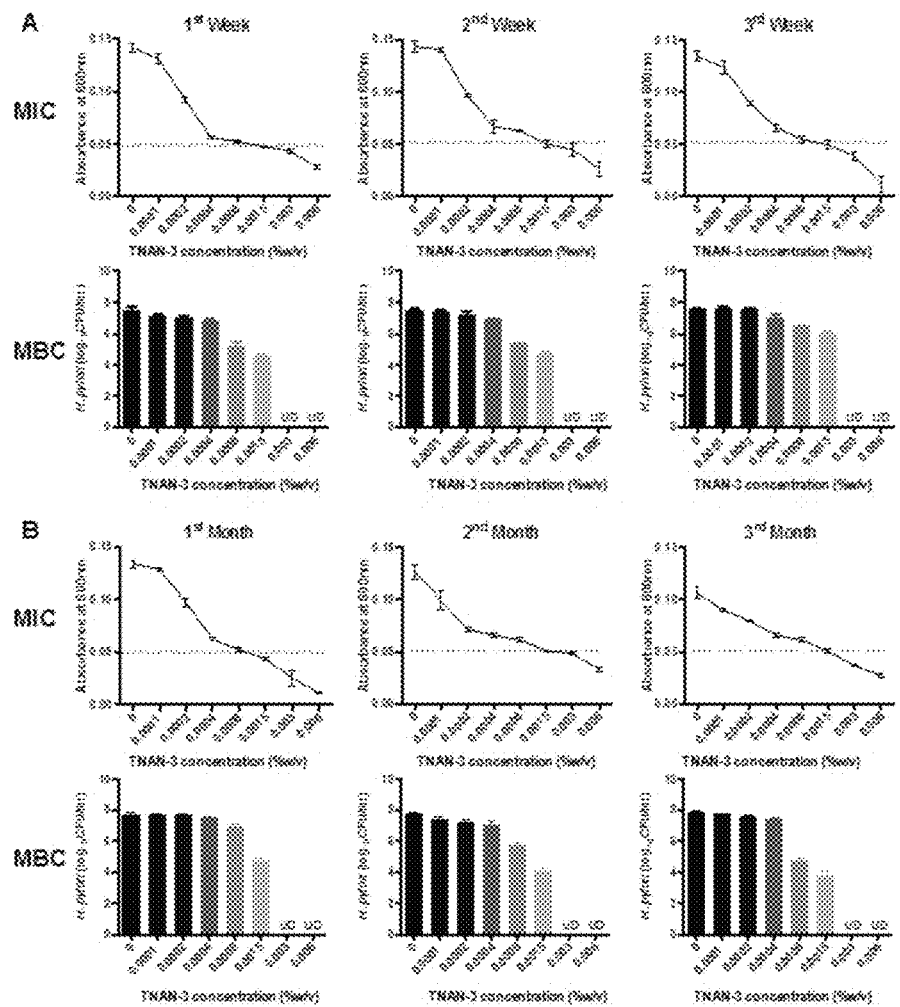
FIG. 23 shows the long-term antibacterial activity of the nanoparticles of the present invention containing 0.3% w/v myristoleic acid. After stored at −20° C. for 3 months in a lyophilized form, the nanoparticles showed MIC and MBC values similar to the freshly prepared nanoparticles.

It is critical for the nanoparticle formulations of the present invention to be able to maintain an effective bactericidal effect over extended periods of storage. To assess such ability, the inventors examined MIC and MBC values of the nanoparticles of the present invention over a three-month storage period. As shown in FIGS. 22 and 23, the nanoparticles of the present invention showed a MIC and MBC value equivalent to that of the freshly prepared sample, regardless of whether it was stored in a suspension at room temperature for 3 months or in a freeze-dried form at −20° C. for 3 months.

Figure 7:
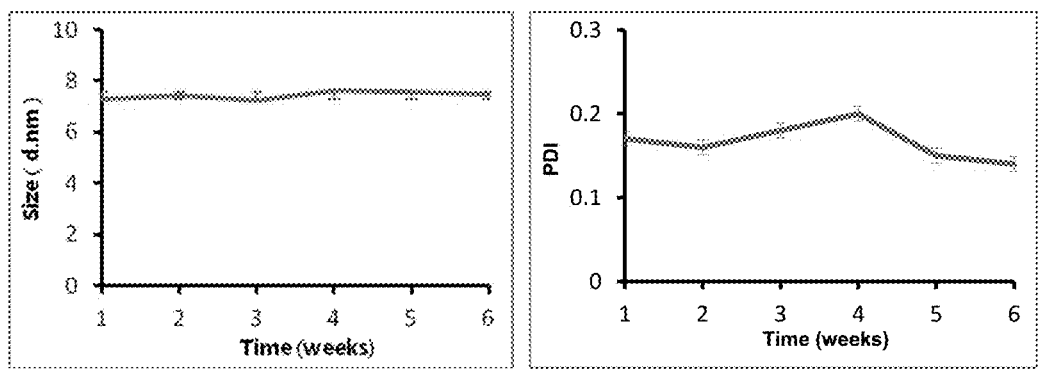
FIG. 7 shows the stability of the nanoparticles of the present invention (comprising 0.4% w/v lauric acid monoglyceride), and the size of the nanoparticles maintained stably over a 6 week period of detection.

It also exhibits excellent storage stability for the nanoparticles of the invention comprising lauric acid monoglyceride. The present inventors stored the nanoparticles of the present invention containing 0.4% w/v lauric acid monoglyceride at room temperature for 6 weeks. Changes in the stability can be tested by detecting the particle size. As shown in FIG. 7, the particle size of the nanoparticles of the present invention stored at room temperature for 6 weeks remained between 7.5 and 8.0 nm, and the change in particle size can be almost negligible, indicating high stability of the nanoparticles of the present invention under such storage condition.

Example 4-1. In Vivo Antibacterial Efficacy of the Nanoparticles of the Invention-1

Figure 24:
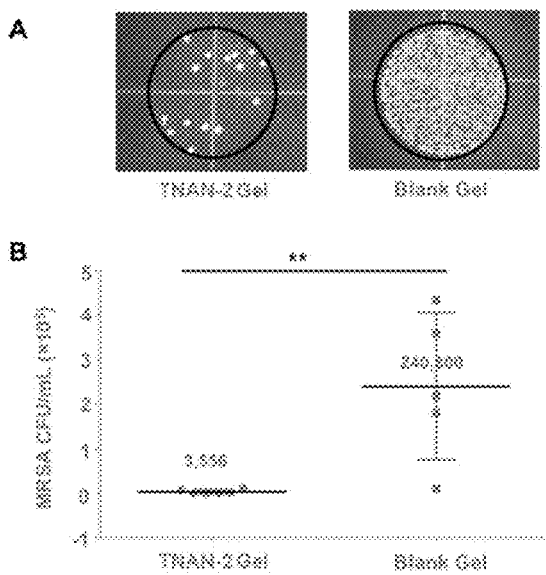
FIG. 24 shows in vivo antibacterial activity of the nanoparticles of the invention containing 1% w/v linolenic acid against MRSA252. Mice were infected with 1*10⁷ CFU of MRSA252. And then the gel containing the nanoparticles of the present invention was used once daily for 5 consecutive days. After MRSA252 was inoculated for 5 days, the infected skin on the mice was removed, homogenized and grown on agar plates to record bacterial CFU. The data show the mean±standard deviation of six separate experiments. * Represents significance of p-value (** $p < 0.01$).

In vivo antibacterial activity and therapeutic effects of the nanoparticles of the invention (1% w/v linolenic acid) against MRSA252 infection were further evaluated by using skin abrasion infection model of ICR mice. (Mouse) infection was caused by MRSA252, and gel of the nanoparticles of the invention and blank gel were applied daily for 5 consecutive days. Bacterial load was measured on the 6th day after MRSA252 infection. Skin tissue was firstly homogenized in PBS and incubated overnight on MRSA-specific agar plates (mannitol agar). Mannitol agar plates were specifically selected for MRSA culture since agar color changes from pink to yellow with the growth of MRSA. As shown in FIG. 24A, the MRSA agar plates treated by the nanoparticles of the present invention remained pink, while those plates in the control group (using a blank gel) turned yellow. This observation means that the nanoparticle of the present invention has a strong bactericidal activity at the skin abrasion infection. In addition to the visual observation, the present inventors further calculated the CFU value of the sample. The results showed that the amount if bacteria remained on the blank gel-treated mouse skin was about 66 times that on the skin treated by the nanoparticle of the present invention, with the hypothesis value of t-distribution test being less than 0.01 (FIG. 24B).

To better assess the anti-MRSA activity of the nanoparticles of the present invention, the nanoparticles were further tested in a model of subcutaneous infection of ICR mice. In this study, 24 hours after infection, blank gel-treated mice showed a purulent lesion at the site of infection. The mice treated by the nanoparticle gel of the present invention showed a rash near the infection site but were of much less severity (FIG. 25). After 72 hours, lesions in the blank gel-treated mice became more pronounced, implying distribution of the infection in mice. In contrast, the mice treated by the nanoparticle gel of the present invention showed insignificant lesions. This comparison shows the superior anti-MRSA efficacy of the nanoparticles of the present invention.

Example 4-2. In Vivo Antibacterial Efficacy of the Nanoparticles of the Invention-2

Figure 29:
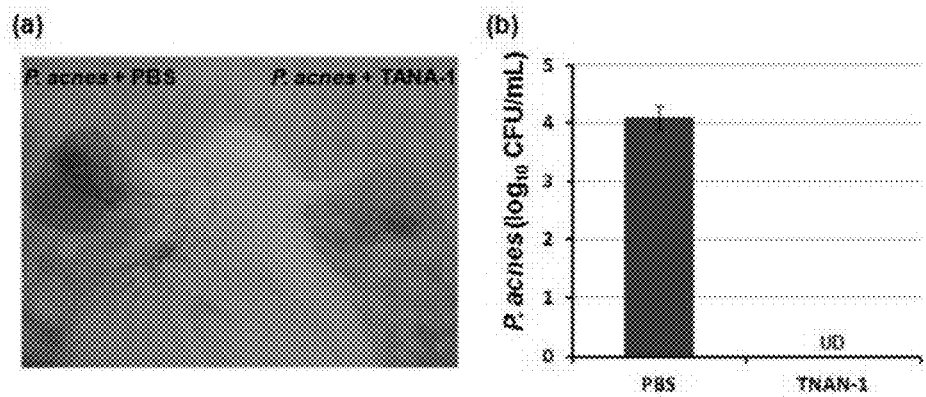
FIG. 29 shows in vivo antibacterial activity of nanoparticles of the invention (1% w/v of lauric acid) against *P. acnes* using a mouse ear model. The ears (left and right ears) of ICR mice were intradermally injected with *P. acnes* (1×10⁷ CFU in 20 μL of PBS). Nanoparticles of the invention (1 wt % lauric acid) or PBS were injected at the site where *P. acnes* was injected, respectively. After twenty-four hours, skin tissue contaminated with bacteria was removed for bacterial count. (a) Tissue injury at the injection site 24 hours after injection. (b) Microbial load at injection site 24 hours after injection (UD: undetectable).

ICR mice were intradermally injected to test in vivo antibacterial activity of the nanoparticles of the present invention (1% w/v lauric acid) against *P. acnes*. In this example, mouse's ear was selected for intradermal injection since the structure of the ear can remain inoculated bacteria in the injection area. To test the antibacterial activity of the nanoparticles of the present invention against *P. acnes* in physiological environments, *P. acnes* (1×10 CFU in 20 μL PBS) was intradermally injected in both ears (left and right ears) of ICR mice. The *P. acnes*-injected site was then injected with the nanoparticles of the invention (1% w/v lauric acid) or PBS (used as a negative control). After 24 hours, samples of mouse ear were collected by 8-mm diameter biopsies perforation and then homogenized and cultured to count remaining *P. acnes*. As shown in FIG. 29, *P. acnes* inoculated on mouse's ears can be completely eliminated using the nanoparticle of the present invention. In contrast, in the negative control (PBS buffer treatment), the number of bacteria was detected as $1.2\times10^4$ CFU/mL. The above results demonstrate that the nanoparticles of the present invention are effective in killing *P. acnes* under physiological environments (e.g., in dermis).

Example 5-1. Toxicity of the Nanoparticles of the Present Invention to Normal Skin Tissue-1

The toxicity of the nanoparticles of the present invention was tested by topical application of the gel formulation of the nanoparticles of the invention (1% w/v linolenic acid) to the epidermis of shaved mice within 5 days. As shown in FIG. 26, no erythema or edema or irritation caused by the nanoparticles of the present invention was found.

To further assess irritation and apoptosis, H & E staining and terminal deoxynucleotidyl transferase labeling (TUNEL) assays were performed. As shown in FIG. 27, the skin surface treated by the nanoparticles of the present invention maintained an undestroyed structure with a clear layer of healthy epidermal cells above the dermis, which was identical to the untreated skin sample. H & E staining also demonstrated that compared with the untreated skin, treatment by the nanoparticles of the invention did not cause any intra-tissue inflammation. In addition, TUNEL analysis was performed to assess severe DNA damage produced in skin tissue and the amount of necrotic cell. In FIG. 27, compared with untreated skin, the skin tissue treated by the nanoparticles of the present invention did not show significant increase in apoptotic staining.

Figure 28:
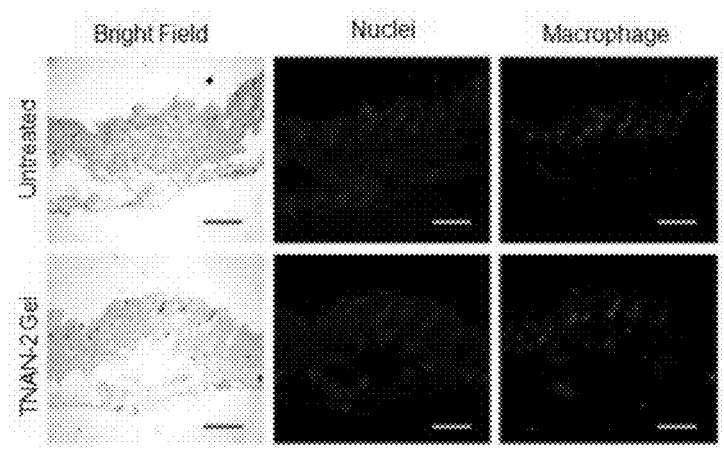
FIG. 28 shows the evaluation of macrophage infiltration on the skin. The safety of using the nanoparticles of the invention containing 1% w/v linolenic acid was evaluated. Frozen sections of the skin were prepared, and then nuclei were stained with DAPI and skin macrophages were stained with FITC-anti-mouse f4/80 antibody. Immediately after staining, skin samples were imaged using Nikon Delta Macroview fluorescence microscope. Images are representative of 5 mice in each group. The scale in pictures is 400 μm.

To further verify the safety of the nanoparticles of the present invention, in particular whether it causes skin inflammation, we measured the level of skin-infiltrating macrophages. In this study, dermal macrophages untreated and treated by the nanoparticles of the present invention in skin tissue were stained with FITC-anti-mouse f4/80 antibody. As shown in FIG. 28, skin macrophages can be observed in the lower part of the epidermis above the dermal layer, and the treatment by the nanoparticles of the present invention did not change such tissue distribution. Compared with untreated skin samples, samples treated with the nanoparticles of the present invention did not show a significant increase in infiltrating macrophages, indicating no significant inflammation.

Example 5-2. Toxicity of the Nanoparticle of the Present Invention to Normal Skin Tissue-2

Figure 30:
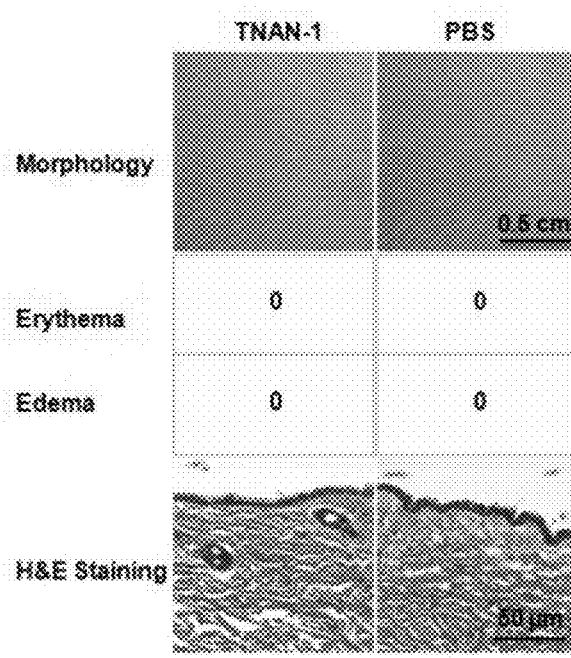
FIG. 30 shows results of toxicity testing of the nanoparticles of the invention (1% w/v lauric acid) on the back skin of mice. Nanoparticles of the invention in a form of gel were applied to the shaved back skin of mice. After 24 hours the gel was removed and the skin was analyzed. The skin treated with nanoparticles of the present invention retained normal structure and no erythema or edema was observed. Results from Hematoxylin & Eosin staining (H & E) showed that the skin treated with nanoparticles of the present invention was structurally intact with a layer of healthy epidermal cells on the dermis. The observed results of treatment with nanoparticles of the invention were the same as those treated with PBS, indicating that the nanoparticles of the invention did not cause detectable toxicity to the skin.

Following topical application of a gel of the nanoparticles of the invention (1% w/v lauric acid) on the back skin of ICR mice, the possible toxicity of the nanoparticles to normal skin tissue was detected by examining changes in skin morphology. In this example, the back skin of the mice was shaved 24 hours before dosing so that there was enough time for the stratum carneum to recover from possible scratches. And the skin was wetted with PBS prior to the experiment. Samples of the nanoparticles of the present invention were then topically applied to the skin, the drug was removed after 24 hours and and the skin was washed and wetted with PBS. As shown in FIG. 30, the skin treated by the nanoparticles of the present invention retained normal structure with no erythema or edema. The structure of nanoparticle-treated skin was similar to that of the negative control, i.e., structure of blank PBS gel-treated skin. According to Draize's Scoring System on Skin Irritation, the erythema and edema of the skin treated by the nanoparticles of the present invention were scored as 0, indicating no apparent skin irritation. Skin biopsy samples were collected and histologically examined and analyzed using hematoxylin and eosin (H & E) staining. The results (FIG. 30, lower part) show that the skin treated by the nanoparticle of the present invention was structurally intact with a layer of healthy epidermal cells on dermis, which was identical with the result from PBS. This result further confirms the safety of using the nanoparticles of the present invention.

Figure 31:
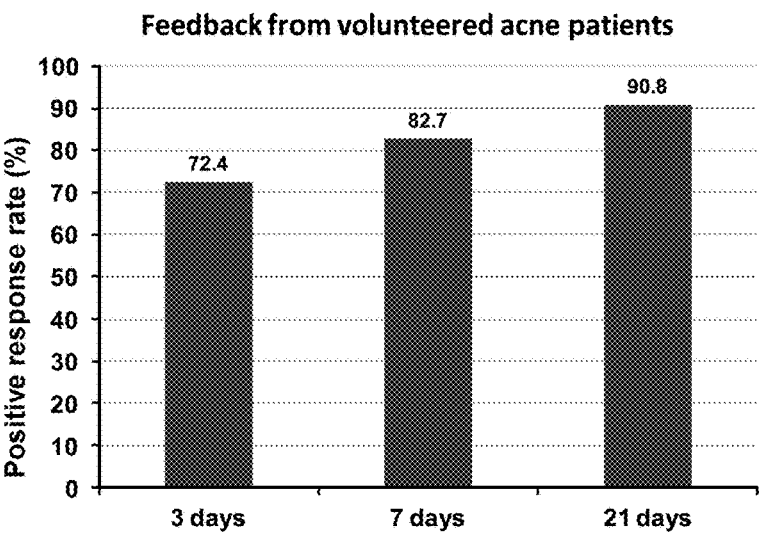
FIG. 31 shows the feedback results from 98 acne volunteers using the nanoparticle gel of the present invention. Feedback results were collected on day 3, day 7 and day 21, respectively.
Figure 32:
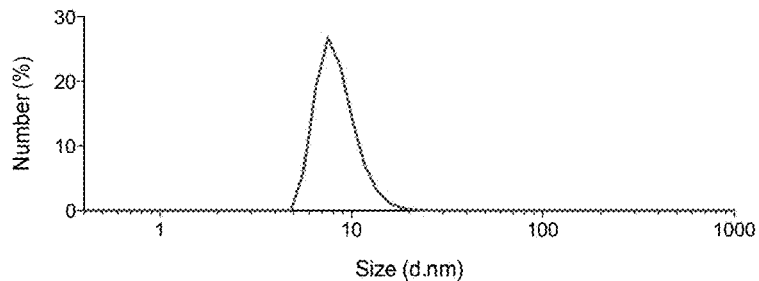
FIG. 32 shows the size distribution curves of the nanoparticles of the invention containing 1% w/v linolenic acid.
Figure 33:
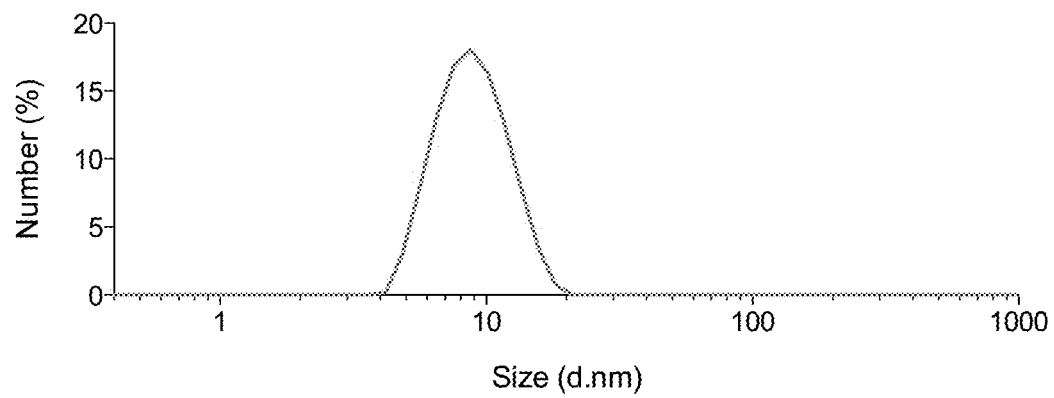
FIG. 33 shows the size distribution curve of the nanoparticles of the invention (1% w/v lauric acid).

Example 6. Human Testing of the Nanoparticles of the Invention 98 volunteers were enrolled for using a gel of the nanoparticles of the invention (1% w/v lauric acid), and the volunteers had different stages of acne infection. The gel was used twice daily for 3 weeks. Feedback from the users was collect on days 3, 7 and 21. The statistical results show that, on days 3, 7 and 21, there were 72.4%, 82.7% and 90.8% of the users gave positive and affinitive evaluation on effects of the gel of the nanoparticles of the present invention, respectively (FIG. 31). The feedback provided by the volunteers showed that the nanoparticles of the present invention are effective in reducing or eliminating acne infections caused by *P. acnes*.

Example 7. Antimicrobial Action of Fatty Acids in Aqueous System

The present inventors further tested the antibacterial activity of the nanoparticles of the present invention and free fatty acids in an aqueous system.

Figure 36:
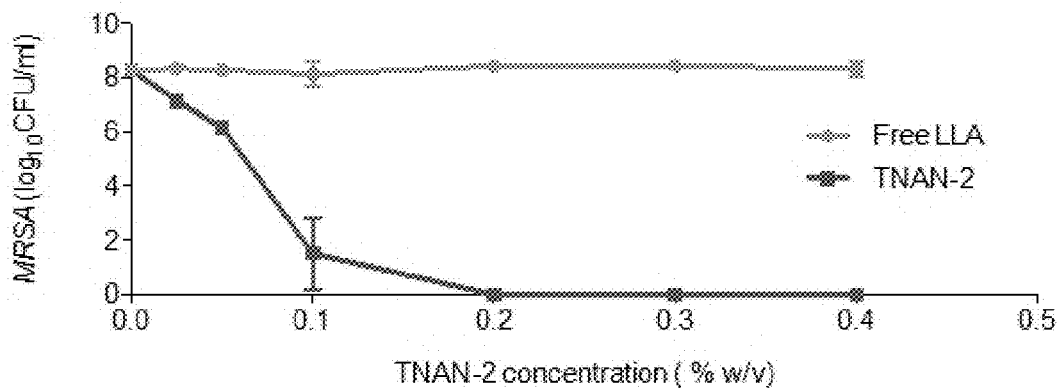
FIG. 36 compares the minimum bactericidal concentration of nanoparticles of the invention containing 1% w/v linolenic acid with that of free fatty acids in an aqueous environment.
Figure 37:
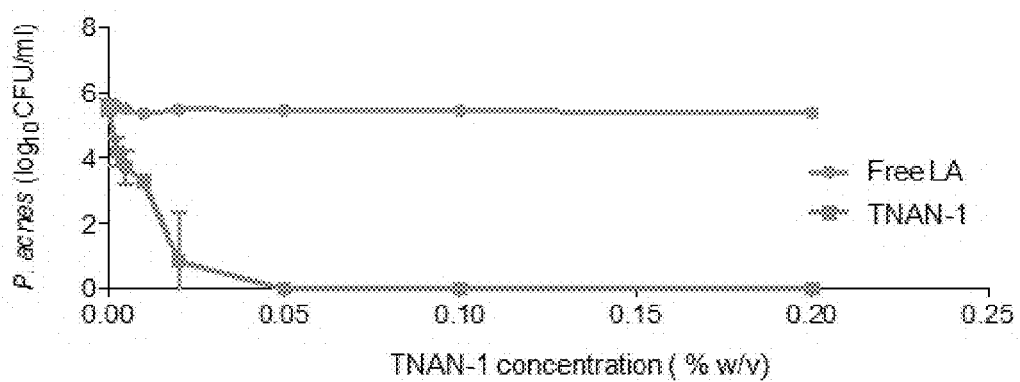
FIG. 37 compares the minimum bactericidal concentration of nanoparticles of the invention (1% w/v lauric acid) with that of free fatty acids in an aqueous environment.
Figure 38:
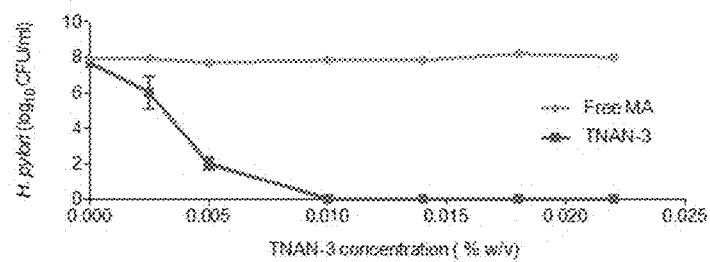
FIG. 38 shows that free myristoleic acid in PBS buffer does not exhibit activities against *H. pylori* but myristoleic acid (0.3% w/v) in a form of nanoparticles of the present invention exhibits activities against *H. pylori*.

Results are shown in FIGS. 36-38. In an aqueous system (PBS), the nanoparticles of the invention containing linolenic acid can significantly kill MRSA, whereas free linolenic acid had almost no bactericidal effect in an aqueous system;

The nanoparticles of the invention comprising lauric acid can significantly kill *Propionibacterium acnes*, whereas free lauric acid has almost no bactericidal effect in an aqueous system;

Myristoleic acid in a form of nanoparticles of the present invention showed bactericidal activity against *H. pylori*, while a free form of myristoleic acid at the same concentration did not show bactericidal activity against *H. pylori*.

This demonstrates that fatty acids can exert their antibacterial effects only if free fatty acids are prepared in a form of nanoparticles of the invention.

All references mentioned in the present application are incorporated herein by reference, as if each reference was individually incorporated by reference. In addition, it should be understood that after reading the above teachings of the present invention, a skilled person can make various modifications or changes to the present invention, and such equivalent forms also fall within the scope of the appended claims of the present application.

The invention claimed is:

1. A non-vesicular nanoparticle, consisting of a fatty acid or a derivative thereof, a surfactant, and optionally a lipid, wherein:
   the particle size of the nanoparticle is 5-20 nm;
   the fatty acid is linolenic acid, lauric acid, or myristoleic acid;
   the derivative of a fatty acid is lauric acid monoglyceride;
   the surfactant is one or more selected from the group consisting of Polysorbate 20 and polysorbate 80;
   the lipid is egg yolk lecithin and cholesterol at a weight ratio of 9:1;
   the concentration of the fatty acid or a derivative thereof is 0.3 to 3% w/v;
   the mass ratio of the lipid to the surfactant is 2.5~0:1; and
   the non-vesicular nanoparticle is prepared by a method comprising:
   1) suspending the surfactant and optionally the lipid in water;
   2) stirring the resulting suspension from 1) until a homogeneous suspension is formed;
   3) heating the resulting homogeneous suspension from 2) to a temperature above the melting point of the surfactant and optionally the lipid contained therein;
   4) adding the fatty acid or the derivative of a fatty acid into the hot suspension obtained in 3) and stirring;
   5) cooling and standing the resulting suspension from 4) to obtain a suspension comprising the non-vesicular nanoparticle.

2. The non-vesicular nanoparticle of claim 1, wherein the particle size of the nanoparticle is 5-15 nm.

3. The non-vesicular nanoparticle of claim 1, wherein the polydispersity index of a plurality of nanoparticles is <0.3.

4. The non-vesicular nanoparticle of claim 3, wherein the polydispersity index of a plurality of the nanoparticles is <0.2.

5. A pharmaceutical composition, comprising the non-vesicular nanoparticle of claim 1 and, optionally, a pharmaceutically acceptable carrier.

6. The pharmaceutical composition of claim 5, wherein the pharmaceutical composition further comprises other antibiotics.

7. The pharmaceutical composition of claim 5 or 6, wherein the pharmaceutical composition is an aqueous pharmaceutical composition.

8. A method for preparing the non-vesicular nanoparticle of claim 1, comprising the following steps:
   1) suspending a surfactant and optional lipid in water;
   2) stirring the resulting suspension from 1) until a homogeneous suspension is formed;

3) heating the resulting homogeneous suspension from 2) to a temperature above the melting point of the surfactant and optional lipid contained therein;
4) adding a fatty acid or a derivative thereof into the hot suspension obtained in 3) and stirring;
5) cooling and standing the resulting suspension from 4) to obtain the non-vesicular nanoparticle.

* * * * *